United States Patent [19]
Arrowsmith et al.

[11] Patent Number: 5,776,951
[45] Date of Patent: Jul. 7, 1998

[54] ANTI-ATHEROSCLEROTIC DIARYL COMPOUNDS

[75] Inventors: Richard James Arrowsmith; John Gordon Dann; Karl Witold Franzmann; Simon Teanby Hodgson; Peter John Wates, all of Beckenham, Great Britain

[73] Assignee: Glaxo Wellcome Inc., Research Triangle Park, N.C.

[21] Appl. No.: 564,281

[22] PCT Filed: Jun. 29, 1994

[86] PCT No.: PCT/GB94/01409

§ 371 Date: Apr. 11, 1996

§ 102(e) Date: Apr. 11, 1996

[87] PCT Pub. No.: WO95/01326

PCT Pub. Date: Jan. 12, 1995

[30] Foreign Application Priority Data

Jun. 30, 1993 [GB] United Kingdom .................... 9313459
Mar. 25, 1994 [GB] United Kingdom .................... 9406005

[51] Int. Cl.$^6$ ........................................................ A01N 43/40
[52] U.S. Cl. .................... 514/328; 514/237.5; 514/330; 514/399; 514/450; 514/459; 514/456; 514/519; 514/546; 514/603; 514/619; 514/646; 544/165; 546/220; 546/225; 548/338.1; 549/28; 549/23; 549/352; 560/48; 564/86; 564/163; 564/430
[58] Field of Search ................... 514/237.5, 328, 514/330, 399, 450, 456, 459; 544/165; 546/220, 225; 548/338.1; 549/23, 28, 352

[56] References Cited

U.S. PATENT DOCUMENTS 5,385,912 1/1995 Neuenschwander et al. .......... 514/305
5,395,853 3/1995 Jackson et al. ........................ 514/596

FOREIGN PATENT DOCUMENTS 272944 12/1991 Czechoslovakia .
253310 1/1988 European Pat. Off. .
A-0 370 740 5/1990 European Pat. Off. .
1377315 12/1974 United Kingdom .
WO93/15046 8/1993 WIPO .

OTHER PUBLICATIONS

Jilek et al., *Collect. Czech. Chem. Commun.*, 54(12), 3294–3339, 1989.

Watanabe et al., *J. Org. Chem.*, 49(5), 742–747, 1984.

Adzima et al., *J. Am. Chem. Soc.*, 100(3), 953–962, 1978.

Boruffini et al., *Farmaco Ed. Sci.*, 26(10), 8910907, 1971.

*Primary Examiner*—C. Warren Ivy
*Assistant Examiner*—Garth M. Dahlen
*Attorney, Agent, or Firm*—Bacon & Thomas

[57] ABSTRACT

The present invention is concerned with diaryl compounds of formula (I) and their use in medical therapy, particularly in the prophylaxis or treatment of a clinical condition for which an ACAT inhibitor is indicated, such as hyperlipidaema or atherosclerosis. The invention also relates to pharmaceutical compositions and processes for the preparation of compounds according to the invention.

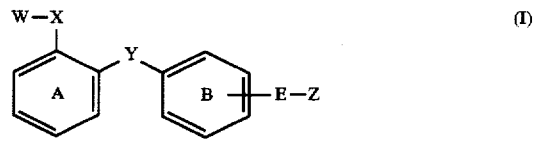

11 Claims, No Drawings

ANTI-ATHEROSCLEROTIC DIARYL COMPOUNDS

This application is a 371 of PCT/GB94/01409 filed Jun. 29, 1994.

The present invention is concerned with diaryl compounds, processes for their preparation, compositions containing them and their use in medicine, particularly in the prophylaxis and treatment of atherosclerosis.

The deposition of cholesterol and cholesteryl esters in atherosclerotic lesions is one of the principal pathological processes of atherogenesis. The enzyme acyl coenzyme A: cholesterol acyltransferase (ACAT) catalyses the synthesis of cholesteryl esters and is thought to play an important role in the regulation of intracellular cholesterol metabolism. Inhibition of ACAT is therefore expected to reduce the content of cholesteryl esters within the lesion and to render the lesion less capable of provoking a thrombotic event. To achieve inhibition of lesion ACAT, a suitable compound would clearly need to be systemically bioavailable.

ACAT may also play a key role in the gastrointestinal absorption of cholesterol on the basis that (a) more than 90% of the cholesterol which appears in the lymph is esterified, (b) substantial ACAT activity has been observed in the intestinal mucosal cells of several animal species, (c) the site of greatest intestinal ACAT activity is the jejunum where the majority of cholesterol absorption occurs, (d) ACAT activity in the jejunum parallels increases in dietary cholesterol. A likely consequence of inhibiting cholesterol absorption in the gut will be a reduction in plasma cholesterol concentration. There is also evidence that a systemically-available ACAT inhibitor may lower plasma cholesterol by reducing the secretion of very low density lipoprotein by the liver. ACAT inhibitors are known to decrease the absorption of cholesterol from the gut and to lower the concentration of total plasma cholesterol in a range of animal models.

European Patent Specification 0370740 discloses diaryl compounds having non-systemic ACAT inhibitory activity.

A further class of aryl compounds has now been discovered which are bioavailable and exhibit ACAT inhibitory activity as demonstrated hereinafter in the ACAT inhibition assay in which representative compounds of the present invention have been shown to be active. The compounds of the invention may therefore be particularly useful for decreasing the steady state concentration of cholesterol and cholesterol ester in the arterial wall, thereby retarding and/or reversing the build-up of atherosclerotic lesions as well as being hypolipidaemic.

According to the present invention, therefore, there are provided compounds of formula (I)

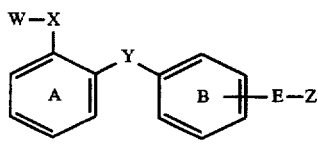

(I)

wherein:

W is hydrogen, or a $C_{1-12}$ hydrocarbyl group optionally substituted by one or more groups independently selected from halo, $C_{1-4}$ alkyl, $C_{1-4}$ alkoxy, hydroxy, $C_{1-4}$ haloalkyl $C_{1-4}$ haloalkoxy, and RC(O)— (wherein R is selected from hydrogen, $C_{1-4}$ alkyl, $C_{1-4}$ alkoxy, hydroxy, $C_{1-4}$ haloalkyl, and $C_{1-4}$ haloalkoxy);

X is —$NR^1C(O)NR^2$—, —$NR^1C(O)O$—, —$NR^1C(O)O$—, —$C(O)NR^2$—, or —$OC(O)NR^2$— (wherein $R^1$ and $R^2$ are independently selected from hydrogen, $C_{1-4}$ alkyl, and $C_{1-4}$ haloalkyl);

Y is a bond, $C_{2-4}$ alkynylene, $C_{2-4}$ alkenylene (cis or trans), $C_{1-4}$ alkylene, —$(CH_2)_n$—O—$(CH_2)_p$—, or —$(CH_2)_n$—$S(O)_q$—$(CH_2)_p$—, (wherein n and p are integers independently selected from 0, 1, 2, 3, and 4; providing that n+p is not greater than 4; and q is an integer selected from 0, 1, and 2), and Y is optionally substituted by one or more groups independently selected from halo, $C_{1-4}$ alkyl, and $C_{1-4}$ haloalkyl;

E is a bond, $C_{1-4}$ alkylene, —$(CH_2)_r$—)—$(CH_2)_s$—, —$(CH_2)_r$—$S(O)_t$—$(CH_2)_s$—, —$(CH_2)_r$—$C(O)$—$(CH_2)_s$— (wherein r and s are integers independently selected from 0, 1, 2, 3 and 4; providing that r+s is not greater than 4; and t is an integer selected from 0, 1, and 2), —$OC(O)$—, —$C(O)O$—, —$S(O)_2N(R^3)$—, —$(R^3)NS(O)_2$—, —$C(O)N(R^3)$—, —$(R^3)NC(O)N(R^4)$—, or —$(R^3)NC(O)$— (wherein $R^3$ and $R^4$ are independently selected from hydrogen, $C_{1-4}$ alkyl, and $C_{1-4}$ haloalkyl);

Z is an aliphatic ring system, $C_{1-8}$ alkyl, $C_{1-8}$ alkoxy, hydroxy, halo, or aryl, and Z is optionally substituted by one or more groups independently selected from halo, cyano, —$CO_2R^6$, —$C(O)NR^6R^7$, —$NR^6R^7$ (wherein $R^6$ and $R^7$ are independently selected from hydrogen, $C_{1-4}$ alkyl, and $C_{1-4}$ haloalkyl), $C_{1-4}$ alkyl, $C_{1-4}$ haloalkyl, $C_{1-4}$ alkoxy, $C_{1-4}$ haloalkoxy, hydroxy, and $C_{2-8}$ polyether.

phenyl rings A and B are optionally substituted by one or more groups independently selected from halo, $C_{1-4}$ alkyl, $C_{1-4}$ haloalkyl, $C_{1-4}$ alkoxy, $C_{1-4}$ haloalkoxy, hydroxy, cyano, $R^8R^9NC(O)$—, $R^8C(O)N(R^9)$—, $R^8C(O)O$—, and $R^8C(O)$— (wherein $R^8$ and $R^9$ are independently selected from hydrogen, $C_{1-4}$ alkyl and $C_{1-4}$ haloalkyl);

provided that if Y is methylene, ethylene, or n-propylene, or —CH=CH— (cis or trans), then group —E—Z is not $C_{1-6}$ alkyl optionally substituted by one or more independently selected polar groups;

or a pharmaceutically acceptable salt, solvate, or physiologically functional derivative thereof for use in medical therapy; particularly, for use in the prophylaxis or treatment of a clinical condition in a mammal, such as a human, for which an ACAT inhibitor is indicated, such as hyperlipidaemia or atheroclerosis.

In the alternative, the present invention provides a method for the prophylaxis or treatment of a clinical condition in a mammal, such as a human, for which an ACAT inhibitor is indicated, such as hyperlipidaemia or atherosclerosis, which comprises the administration to the mammal of a therapeutically effective amount of a compound of formula (I) (as defined above), or a pharmaceutically acceptable salt, solvate, or physiologically functional derivative thereof The term "halo" means fluoro, chloro, bromo, or iodo.

The terms "alkyl", "alkoxy", "alkylene", "alkenyl", "alkenylene", "alkynyl",and "alkynylene" have meaning as understood by the person skilled in the art and include straight and branched chains.

The terms "haloalkyl" and "haloalkoxy" mean respectively an alkyl or alkoxy group as defined above in which one or more of the hydrogen atoms is replaced by a halo group as defined above, and preferably containing one, two or three halo groups selected from fluoro and chloro. Examples of such groups include chloromethyl, trifluoromethyl, chloromethoxy and trifluoromethoxy.

The term "$C_{1-2}$ hydrocarbyl group" means a straight or branched hydrocarbon chain of from 1 to 12 carbon atoms which may contain 1 to 4 double and/or triple bonds, or a $C_{3-8}$ saturated or unsaturated cyclic hydrocarbon which may contain 1 to 4 double and/or triple bonds. Examples include $C_{1-2}$ alkenyl, $C_{2-12}$ alkenyl, $C_{2-12}$ alkynyl, $C_{3-7}$ cycloalkyl, $C_{3-7}$ cycloalkenyl $C_8$ cycloalkynyl, and $C_{7-10}$ aralkyl.

In the definition of Z the term "aryl" means a monovalent aromatic radical derived from a single ring or 2 fused rings of carbon atoms and, optionally 1 to 4 heteroatoms selected from nitrogen, sulphur, and oxygen. Preferably, in the definition of Z, aryl means carbocyclic aryl such as phenyl, and 1-, or 2-naphthyl.

The term "aliphatic ring system" means a non-aromatic system of 1 or 2 rings containing a total of 3 to 10 carbon atoms, which may contain 1 or 2 double and/or triple bonds and optionally one, two or three groups selected from —N($R^5$)— (wherein $R^5$ is selected from hydrogen, $C_{1-4}$ alkyl, and $C_{1-4}$ haloalkyl), —C(O)—, —O—, —S—, —S(O)—, and —S(O)$_2$—. Suitable examples include $C_{4-7}$ cycloalkyl, (for example, cyclopentyl or cyclohexyl), or an oxetane, tetrahydrofuran, tetrahydropyran, 1, 3—, or 1, 4-dioxane, 1, 3—, or 1, 4-dioxin, morpholine, 2-oxo-pyrrolidine, 2, 6-dioxo-piperidine, tetrahydrothiopyran, 8-oxabicyclo[3.2.1]octane, 8oxa-3-azabicyclo[3.2.1]octane, or 3-oxo-8-azabicyclo[3.2.1]octane group. Preferably, the aliphatic ring system is a single 5-or 6-membered ring.

The term "$C_{2-8}$ polyether" means a $C_{2-8}$ alkyl group in which one to four non-adjacent —CH$_2$—groups has been replaced by—O—.

The present invention also provides compounds of formula (I) as defined above and salts, solvates, and physiologically functional derivatives thereof, with the provisoes that:

(i) when Y is —S—, X is —NR$^1$C(O)— (wherein R$^1$ is hydrogen or $C_{1-3}$ alkyl), and W is hydrogen or $C_{1-3}$ alkyl, then—E—Z is not methoxy;

(ii) when Y is —S—or —O—, X is —C(O)NH—, W is hydrogen, ring A is unsubstituted or has one substituent selected from $C_{1-4}$ alkyl or $C_{1-4}$ alkoxy, and ring B is unsubstituted or has one to three substituents selected from halogen and alkyl, then—E—Z is not optionally substituted cycloalkyl, halogen, or alkylmercapto;

(iii) the compound of formula (I) is not:
 N,N-diethyl-2-[2-(4-methoxyphenyl)ethenyl] benzamide,
 Bis[2-(N-isopropylcarbamoyl)phenyl]sulphide,
 Bis[2-(N-isopropylcarbamoyl)phenyl]sulphoxide,
 Bis[2-(N-isopropylcarbamoyl)phenyl]sulphone,
 2,2'-thiobis[N,N-bis(1-methylpropyl)benzamide], or
 2,2'-thiobis(N-butylbenzamide).

Preferred examples of W include optionally substituted $C_{3-7}$ alkyl such as, iso-propyl, tert-butyl, n-heptyl, hydroxycarbonylethyl and ethoxycarbonylethyl; more preferably W is $C_{3-5}$ alkyl; most preferably, W is tert-butyl.

Preferred examples of X include —C(O)NR$^2$—, —NR$^1$C (O)—, and —NR$^1$C(O)NR$^2$— (wherein R$^1$ and R$^2$ are as defined for formula (I) and are, for example independently selected from hydrogen and methyl); most preferably, X is —C(O)NH—.

Preferred examples of Y include ethylene, ethenylene, ethenylene, —O—, —S—, —CH$_2$O—, and —OCH$_2$—; more preferably, Y is ethylene, ethenylene, ethenylene, or —O—; most preferably, Y is ethenylene or —O—.

Suitably E is is a bond, $C_{1-4}$ alkylene, —(CH$_2$),—O—(CH$_2$)$_s$, —(CH$_2$)$_r$—S(O)$_t$—(CH$_2$)$_s$—, —(CH$_2$)$_r$—C(O)—(CH$_2$)$_s$— (wherein r and s are integers independently selected from 0, 1, 2, 3 and 4; providing that r+s is not greater than 4; and t is an integer selected from 0, 1, and 2), —S(O)$_2$N(R$^3$)—, —(R$^3$)NS(O)$_2$—, —C(O)N(R$^3$)—, —(R$^3$)NC(O)N(R$^4$)—, or —(R$^3$)NC(O)— (wherein R$^3$ and R$^4$ are independently selected from hydrogen, dC$_{1-4}$ alkyl, $C_{1-4}$ haloalkyl). Preferred examples of E include —O—, —OCH$_2$—, —CH$_2$O—, a bond, —C(O)N(R$^3$)—, —(R$^3$) NC(O)—, —S—, —S(O)—, —S(O)$_2$—, —(R$^3$)NS(O)$_2$—, —S(O)$_2$N(R$^3$)—, —(R$^3$)NC(O)N(R$^4$)—, and—C(O)— (wherein R$^3$ and R$^4$ are as defined for formula (I), and are for example, hydrogen); most preferably, E is —O—, or a bond.

Suitably, Z is an aliphatic ring system, $C_{1-8}$ alkyl, $C_{1-8}$ alkoxy, hydroxy, or aryl and is optionally substituted as described above. Preferably, Z is is a 5-or 6-membered saturated ring optionally containing one, two, or three groups selected from —N(R$^5$)—(wherein R$^5$ is selected from hydrogen, $C_{1-4}$ alkyl, and $C_{1-4}$ haloalkyl), —C(O)—, and —O—, or is $C_{1-4}$ alkyl $C_{1-4}$ alkoxy, hydroxy, or aryl and is optionally substituted as described above. Most preferably, Z is a 5-or 6-membered saturated ring optionally containing one, two, or three groups selected from —N(R$^5$)— (wherein R$^5$ is selected from hydrogen, $C_{1-4}$ alkyl, and $C_{1-4}$ haloalkyl), —C(O)—, and —O—, or is $C_{1-4}$ alkyl, or $C_{1-4}$ alkoxy and is optionally substituted as described above.

Suitably, the substituents on Z are selected from halo, —NR$^6$R$^7$ (wherein R$^6$ and R$^7$ are independently selected from hydrogen, $C_{1-4}$ alkyl and $C_{1-4}$ haloalkyl), $C_{1-4}$ alkyl, $C_{1-4}$ haloalkyl, $C_{1-4}$ alkoxy, $C_{1-4}$ haloalkoxy, hydroxy, and $C_{2-8}$ polyether. Preferably, the substituents on Z are selected from halo, —CO$_2$R$^6$, —C(O)NR$^6$R$^7$, and $C_{1-4}$ alkoxy (wherein R$^6$ and R$^7$ are as defined above).

Suitably, rings A and B are each unsubstituted, or substituted by one to four substituents selected from those described above. Rings A and B are each preferably unsubstituted, or substituted by one or two substituents selected from those described above, most preferably, halo.

The group —E—Z is preferably attached to ring B in a meta or para position relative to group Y; most preferably, in the para position.

Compounds of formula (I) in which:

W is $C_{3-7}$ alkyl optionally substituted as described above;

X is —C(O)NR$^2$—, —NR$^1$C(O)—, or —NR$^1$C(O)NR$^2$— (wherein R$^1$ and R$^2$ are as defined for formula (I));

Y is ethylene, ethenylene, ethenylene, —O—, —S—, —CH$_2$O—, or —OCH$_2$—;

E is —O—, —OCH$_2$—, —CH$_2$O—, a bond, —C(O)N (R$^3$)—, —(R$^3$)NC(O)—, —S—, —S(O)—, —S(O)$_2$—, —(R$^3$)NS(O)$_2$—, —S(O)$_2$N(R$^3$)—, —(R$^3$)NC(O) N(R$^4$)—, or —C(O)—(wherein R$^3$ and R$^4$ are as defined for formula (I)); and Z is a 5-or 6-membered saturated ring optionally containing one, two, or three groups selected from —N(R$^5$)— (wherein R$^5$ is selected from hydrogen, $C_{1-4}$ alkyl, and $C_{1-4}$ haloalkyl), —C(O)—, and —O—, or Z is $C_{1-4}$ alkyl, $C_{1-4}$ alkoxy, hydroxy, or aryl and is optionally substituted as described in formula (I).

and salts, solvates, and physiologically functional derivatives thereof are preferred.

Compounds of formula (I) in which:

W is $C_{3-5}$ alkyl, for example tert-butyl;

X is —C(O)NH—;

Y is ethenylene or —O—;

E is —O—, or a bond;

Z is a 5-or6-membered saturated ring optionally containing one, two, or three groups selected from —N(R$^5$)—

(wherein $R^5$ is selected from hydrogen, $C_{1-4}$ alkyl, and $C_{1-4}$ haloalkyl), —C(O)—, and —O—, or Z is $C_{1-4}$ alkyl, or $C_{1-4}$ alkoxy and Z is optionally substituted as described in formula (I); and the group —E—Z is attached to ring B in the para position relative to group Y; and salts, solvates, and physiologically functional derivatives thereof, are particularly preferred.

Particularly preferred compounds within the scope of formula (I) include:

N-{2,4-Difluoro-6-[4-(1-carbamoyl-1-methylethyl) phenoxy]phenyl}pivalamide;

N-{2,4-Difluoro-6-[4-(2,6-dioxo-4-piperidinyl) phenylethynyl]phenyl}pivalamide;

N-[2-Fluoro-6-(4-trifluoromethoxyphenoxy)phenyl] pivalamide;

N-{2,4-Difluoro-6-[4-4-methoxytetrahydropyranyl) phenylethynyl]phenyl}pivalamide;

N-{2,4-Difluoro-6-[4-2,6-dioxo4-piperidinyl)phenoxy] phenyl}pivalamide;

N-{6-[4-(1-Carbamoyl-1-methylethoxy)phenylethynyl]-2, 4-dilfluorophenyl}pivalamide;

N-{6-[4-(1-Carbamoyl-1-methylethyl)phenylethynyl]-2,4-difluorophenyl}pivalamide;

1-[4-(3-Fluoro-2-pivalamidophenoxy)phenyl]cyclopentane-1-carboxylic acid; and

1-[4-(3-Fluoro-2-pivalamidophenoxy)phenyl]cyclopentane-1carboxamide;

or a salt, solvate, or a physiologically functional derivative thereof

Salts of compounds suitable for use in medicine are those which are pharmaceutically acceptable. However, non-pharmaceutically acceptable salts are within the scope of the present invention for use as intermediates in the preparation of the compounds of the invention and their pharmaceutically acceptable salts, solvates, and physiologically functional derivatives.

Salts according to the invention include ammonium salts, alkali metal salts, such as those of sodium and potassium, alkaline earth metal salts, such as those of calcium and magnesium, salts with organic bases, such as triethanolamine, N-methyl-D-glucamine, piperidine, pyridine, piperazine, and morpholine, and salts with amino acids, such as arginine and lysine. Examples of pharmaceutically acceptable acid addition salts include those derived from mineral acids, such as hydrochloric, hydrobromic, phosphoric, metaphosphoric, nitric, and sulphuric acids, and organic acids, such as tartaric, acetic, trifluoroacetic, citric, malic, lactic, fumaric, benzoic, glycollic, gluconic, succinic and methanesulphonic and arylsulphonic, for example p-toluenesulphonic, acids.

By the term "physiologically functional derivatives" is meant chemical derivatives of compounds-of formula (I) which have the same physiological function as the free compound of formula (I), for example, by being convertible in the body thereto. According to the present invention, examples of physiologically functional derivatives include esters, for example, compounds of formula (I) in which a carboxylic acid or hydroxyl group has been functionalised as an ester. Suitable esters include carboxylic acid esters such as alkyl, cycloalkyl, alkoxyalkyl, optionally substituted aryl and aralkyl esters, sulphonate esters, amino acid esters, and mono-, di-, or tri-phosphate esters. In such esters any alkyl moiety advantageously contains from 1 to 6 carbon atoms, preferably, 1 to 4 carbon atoms; any cycloalkyl moiety advantageously contains from 3 to 6 carbon atoms; and any aryl moiety advantageously comprises a phenyl group.

The amount of a compound of formula (I), or a pharmaceutically acceptable salt, solvate or physiologically functional derivative thereof which is required to achieve the desired therapeutic effect will of course, depend on a number of factors, for example, the specific compound chosen, the use for which it is intended, the mode of adminisration, and the clinical condition of the recipient. In general, a daily dose is expected to lie in the range of from 1 µg to 100 mg, typically from 50 µg to 50 mg, per day per kilogram bodyweight, for example, 0.1–20 mg/kg/day. Unit doses may contain, for example, from 70 µg to 1 g of the active compound. Thus orally administrable unit dose formulations, such as tablets or capsules, may contain, for example, from 3.5 mg to 500 mg, typically from 7 mg to 500 mg. In the case of pharmaceutically acceptable salts, the weights indicated above refer to the weight of the diaryl ion derived from the salt.

The present invention also provides the use of a compound of formula (I), or a pharmaceutically acceptable salt, solvate, or physiologically functional derivative thereof, in the manufacture of a medicament for the prophylaxis or treatment of a clinical condition for which an ACAT inhibitor is indicated, such as hyperlipidaemia or atherosclerosis.

Whilst it is possible for the compounds of formula (I), or pharmaceutically acceptable salts, solvates, or physiologically functional derivatives thereof to be administered alone, it is preferred to present them in the form of a pharmaceutical formulation.

Accordingly, the present invention further provides a pharmaceutical formulation comprising a compound of formula (I), or a pharmaceutically acceptable salt, solvate, or physiologically functional derivative thereof, and a pharmaceutically acceptable carrier or excipient.

The carrier or excipient must, of course, be acceptable in the sense of being compatible with the other ingredients of the formulation and must not be detrimental to the recipient. The carrier or excipient may be a solid or a liquid, or both, and is preferably formulated with the compound as a unit-dose formulation, for example, a tablet, which may contain from 0.05% to 95% by weight of the active ingredient. Other pharmacologically active substances may also be present including other compounds of formula (I) and pharmaceutically acceptable salts, solvates, and physiologically functional derivatives thereof The formulations of the invention may be prepared by any of the well known techniques of pharmacy consisting essentially of admixing the components.

The formulations of the present invention include those suitable for oral, rectal, topical, buccal (e.g. sub-lingual) and parenteral (e.g. subcutaneous, intramuscular, intradermal or intravenous) administration, although the most suitable route in any given case will depend on the nature and severity of the condition being treated and on the nature of the particular compound of formula (I), or a pharmaceutically acceptable salt, solvate, and physiologically functional derivative thereof which is being used.

Hereinafter, the term active ingredient means a compound of formula (I) or a pharmaceutically acceptable salt, solvate, or physiologically functional derivative thereof Formulations suitable for oral administration may be presented in discrete units, such as capsules, cachets, lozenges, or tablets, each containing a predetermined amount of the active ingredient; as a powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association the active ingredient and the carrier or excipient (which may constitute one or more accessory ingredients). In general, the formulations are prepared by uniformly and intimately admixing the active ingredient with a liquid or finely divided solid carrier, or both, and then, if necessary, shaping the product. For example, a tablet may be prepared by compressing or moulding a powder or granules of the active ingredient optionally with one or more assessory ingredients. Compressed tablets may be prepared by compressing, in a suitable machine, the active ingredient in a free-flowing form, such as a powder or granules optionally mixed with a binder, lubricant, inert diluent and/or surface active/dispersing agent(s). Moulded tablets may be made by moulding, in a suitable machine, the powdered active ingredient moistened with an inert liquid diluent.

Formulations suitable for buccal (sub-lingual) administration include lozenges comprising the active ingredient in a flavoured base, usually sucrose and acacia or tragacanth, and pastilles comprising the compound in an inert base such as gelatin and glycerin or sucrose and acacia.

Formulations of the present invention suitable for parenteral administration conveniently comprise sterile aqueous preparations of the active ingredient, preferably isotonic with the blood of the intended recipient. These preparations are preferably administered intravenously, although administration may also be effected by means of subcutaneous, intramuscular, or intradermal injection. Such preparations may conveniently be prepared by admixing the active ingredient with water and rendering the resulting solution sterile and isotonic with the blood. Injectable compositions according to the invention will generally contain from 0.1 to 5% w/w of the active ingredient.

Formulations suitable for rectal administration are preferably presented as unit-dose suppositories. These may be prepared by admixing the active ingredient with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers and excipients which may be used include vaseline, lanoline, polyethylene glycols, alcohols, and combinations of two or more thereof The active ingredient is generally present at a concentration of from 0.1 to 15% w/w of the composition, for example, from 0.5 to 2%.

According to a flurther aspect, the present invention also provides a process for the preparation of compounds of formula (I), or a salt, solvate, or a physiologically functional derivative thereof, which comprises a method well known to those skilled in the art, for example, as described below.

In general, compounds of formula (I) and salts, solvates, and physiologically functional derivatives thereof, may be prepared by coupling a compound of formula (II) with a compound of formula (III);

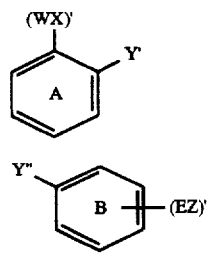

wherein,

Y' and Y" are groups capable of reacting together to form the desired linkage Y (as defined for formula (I)), as discussed below;

(WX)'— is either the group W—X— (wherein W and X are as defined for formula (I)), a protected form thereof or a precursor for the said group W—X—, as discussed below;

—(EZ)' is either the group —E—Z (wherein E and Z are as defined for formula (I)), a protected form thereof or a precusor for the said group —E—Z, as discussed below;

and rings A and B are optionally substituted as described for formula (I)

to give either a compound of formula (I) or a compound of formula (IV):

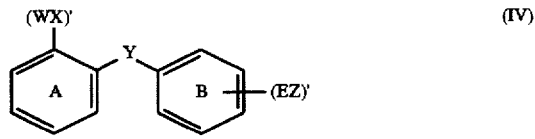

wherein Y is as defined for formula (I), (WX)'— and —(EZ)' are as defined for formulae (I) and (III) respectively (excluding combinations of (WX)'— and —(EZ)' which give a compound of formula (I)), and rings A and B are optionally substituted as described for formula (I);

followed by, (i) When (WX)'— in the compound of formula (IV) is a precursor for the group W—X—, formation of the group W—X— (wherein W and X are as defined for formula (I)), as discussed below; and/or (ii) When —(EZ)' in the compound of formula (IV) is a precursor for the group —E—Z; formation of the group —E—Z (wherein E and Z are as defined for formula (I)), as discussed below, and/or (iii) Removal of any protecting groups; and/or (iv) Optional formation of a salt, solvate, or physiologically functional derivative of the resulting compound of formula (1), as did below or conversion to a different compound of formula (I).

When Y in the compound of formula (I) is to be a bond; Y' and Y" are groups capable of reacting together to provide a direct bond between ring A of the compound of formula (I) and ring B of the compound of formula (III). Suitably, one of Y' and Y" may be —B(OH)₂, and the other a leaving group, for example a halo group (typically bromo or iodo) or a sulphonate such as an alkylsulphonate (typically, methylsulphonate), an arylsulphonate (typically, tolylsulphonate), or a haloasulphonate (typically, trifluoromethanesulfonate); the coupling could then be effected under the conditions described in Tetrahedron Lett., 1987, 28, 5093, for example, in the presence of a suitable catalyst, for example, tetrakis (triphenylphosphine) palladium (0) and an inorganic base, for example, sodium carbonate at elevated temperature, such as 50°–150°C. Alternatively, one of Y' and Y" may be an organometallic group, for example, —MgX' or —ZnX where X is a halogen, and the other a leaving group (as defined above); the coupling could then be effected by analogy with the teaching of Tetrahedron Lett., 1980, 21, 845, Chem. Lett. 1975, 133, and Synth. Commun., 1991, 21, 481, for example, in an inert solvent, such as, TBF, in the presence of a catalyst, such as, 1,4-bis (diphenylphosphine)butane palladium (0) dichloride, palladium acetate, or tetrakistriphenyl phosphine palladium (0), at non-extreme temperature, such as 0°–600° C.

When Y in the compound of formula (I) is to be —(CH₂)ₙ—O—(CH₂)ₚ— or —(CH₂)ₙ—S—(CH₂)ₚ— (wherein n and p are as defined for formula (I)); Y' and Y"

are groups capable of reacting together to provide such a linkage between ring A of the compound of formula (II) and ring B of the compound of formula (III). Suitably, one of Y' and Y" may be —$(CH_2)_n$—L (wherein n is as defined for formula (I) and L is a leaving group as defined above), and the other a—$(CH_2)_p$—OH or —$(CH_2)_p$—SH group (wherein p is as defined for formula (I)); such a reaction could be effected by treatment with a base, such as a hindered base, for example potassium tert-butoxide, or a metal hydride, for example, sodium hydride, in an aprotic solvent, for example N,N-dimethylformamide at a non-extreme temperature, such as, -10° C. to 50° C.

When Y in the compound of formula (I) is to be —$(CH_2)_n$—S(O)—$(CH_2)_p$— or —$(CH_2)_n$—S(O)$_2$—$(CH_2)_p$— (wherein n and p are as defined for formula (I)) the process may be the same as that described above for when Y is —$(CH_2)_n$—S—$(CH_2)_p$— followed by oxidation of the linking sulphur, suitably by treatment with a peroxygen compound, for example, m-chloroperbenzoic acid in an inert solvent, for example, dichloromethane at low temperature, such as -50° C. to 50° C.

When Y in the compound of formula (I) is to be $C_{1-4}$ alkynylene; Y' and Y" are groups capable of reacting together to form such a linkage between ring A of the compound of formula (II) and ring B of the compound of formula (III). For example, when Y in the compound of formula (I) is to be —C≡C—, one of Y' and Y" may be —C≡CH and the other a leaving group (as defined above); the coupling may be effected in the presence of a catalyst system, for example, palladium (O) tetra (triphenylphosphine)/copper (I) iodide/triphenylphosphine, in the presence of an organic base, such as piperidine or a trialkylamine, for example triethylamine, at non-extreme temperature, such as -10° C. to 50° C. Other alkynylene linkages may be formed using the appropriate compounds of formulae (II) and (III) as would be apparent to the person skilled in the art.

When Y in the compound of formula (I) is to be $C_{1-4}$ alkenylene or $C_{1-4}$ alkylene the process may be the same as that described above for when Y is $C_{1-4}$ alkynylene, followed by reduction under suitable conditions, such as chemical or catalytic hydrogenation, for example, treatment with a transition metal catalyst, for example, palladium dibenzyladine acetone ($Pd(dba)_2$), in an aprotic solvent, for example, dimethylsulphoxide, or treatment with $H_2$ in the presence of an inert solvent and a hydrogenation catalyst, for example, palladium on charcoal, at a non-extreme temperature, such as -10° C. to 50° C.

Conversion (i) may be effected in a number of ways, depending on the nature of group X in the compound of formula (I):

(a) When X is to be —$NR^1C(O)NR^2$— (wherein $R^1$ and $R^2$ are as defined for formula (I)), the group (WX)'— in the compound of formula (II) is suitably an isocyanate (O=C=N—) group. The compound of formula (IV) formed after reaction with the appropriate compound of formula (III) may then be treated with a compound of formula W—$NHR^1$ (wherein W and $R^1$ are as defined for formula (I)), typically in a non-polar solvent, for example tetrahydrofuran or benzene, in the presence of an organic base, for example N,N-dimethylaminopyridine (DMAP), at a moderate temperature, for example, in the range 10° C. to 50° C., suitably at ambient temperature. The resulting urea group may optionally be N-alkylated according to conventional methods to give the desired W—$NR^1C(O)NR^2$—group (wherein W, $R^1$, and $R^2$ are as defined for formula (I));

(b) When X is to be —$NR^1C(O)$— or —$C(O)NR^2$— (wherein $R^1$ and $R^2$ are as defined for formula (I)), the group (WX)'—in the compound of formula (II) is suitably a carboxylic acid derivative i.e. LC(O)— (wherein L is a leaving group as defined above) or an amine ie $HNR^2$— (wherein $R^2$ is as defined for formula (I)). The compound of formula (IV) formed after reaction with the appropriate compound of formula (III) may then be treated with a compound of formula W—$NR^1H$ or W—C(O)L respectively (wherein W and $R^1$ are as defined for formula (I) and L is a leaving group as defined above), typically in a non-polar solvent, for example, a halogenated hydrocarbon, such as dichloromethane, an ether, or acetonitrile; in the presence of an organic base, for example, pyridine, DMAP, or a trialkylamine such as triethylamine, at a moderate or reduced temperature, for example, in the range -30° C. to 50° C., suitably at ambient temperature or below (c) When X is to be —$NR^1C(O)O$— or —$OC(O)NR^2$— (wherein $R^1$ and $R^2$ are as defined for formula (I)), the group (WX)'— in the compound of formula (II) is suitably a hydroxyl group or an isocyanate group respectively. The compound of formula (IV) formed after reaction with the appropriate compound of formula (III) may then be treated with a compound of formula W—N=C=O or W—OH respectively (wherein W is as defined for formula (I)), typically under the conditions described in part (a) above. The resulting urethane group may optionally be N-alkylated according to conventional methods to give the desired W—$NR^1C(O)O$— or W—$OC(O)NR^2$— group (wherein W, $R^1$, and $R^2$ are as defined for formula (I)).

Conversion (ii) may be effected in a number of ways, depending on the nature of group E in the compound of formula (I):

(d) When E is to be a bond or C14 alkylene, the group —(EZ)' in the compound of formula (III) is suitably a halogen. The compound of formula (IV) formed after reaction with the appropriate compound of formula (II) may then be treated with a strong base such as butyllithium, in a non-polar solvent, for example tetrahydrofuran, at low temperature, for example -90° C. to -50° C., to form an anion on ring B. The anion may then be treated in situ with a compound contaning an electrophilic ire, such as a ketone, which on reaction with the anion forms the desired group —E—Z (as defined for formula (I)). For example, when the group —E—Z is to be 4-hydroxytetrahydropyran-4-yl, the anion on ring B may be reacted with tetrahydro-4H-pyran4one; in a non-polar solvent, such as tetrahydrofuran; at reduced temperate, for example -90° C. to -50° C.;

(e) When E is to be —$(CH_2)_r$—O—$(CH_2)_s$ or —$(CH_2)_r$S—$(CH_2)_s$—(wherein r and s are as defined for formula (I)), the group —(EZ)' in the compound of formula (III) is suitably —$(CH_2)_r$OH or —$(CH_2)_r$SH (wherein r is as defined above), or a protected form thereof The compound of formula (IV) formed after reaction with the appropriate compound of formula (II) may then be treated with a compound of formula L—$(CH_2)_s$—Z (wherein L is a leaving group, as defined above, and s and Z are as defined for formula (I)), this reaction may be effected in conditions analogous to those described above for the formation of linkage Y, when Y is to be —$(CH_2)_n$—O—$(CH_2)_p$— or —$(CH_2)_n$—S—$(CH_2)_p$— (wherein Y, n, and p are as defined for formula (I));

(f) When E is to be —$(CH_2)_r$—S(O)—$(CH_2)_s$or —$(CH_2)_r$S(O)$_2$—$(CH_2)_s$— (wherein r and s are as defined for formula (I)) the process may be the same as that described above for when E is —(CH$_2$)$_r$—S—(CH$_2$)$_s$—, followed by oxidation of the linking sulphur, suitably by treatment with a peroxygen compound, for example, m-chloroperbenzoic acid in an inert solvent, for example, dichloromethane;

(g) When E is to be —(CH$_2$)$_r$—C(O)—(CH$_2$)$_s$— (wherein r and s are as defined for formula (I)), the group —(EZ)' in the compound of formula (III) is suitably —(CH$_2$)$_r$C(O)L (wherein r is as defined for formula (I) and L is a leaving group as defined above). The compound of formula (IV) formed after reaction with the appropriate compound of formula (II) may then be reacted with an anion of formula —(CH)$_s$—Z (wherein s and Z are as defined for formula (I)), typically in situ after formation of the anion by treatment of the corresponding organic halide with a strong base such as butyl lithium, in a non-polar solvent, for example tetrahydrofuran, at low temperature, for example –90° C. to –50° C.;

(h) When E is to be —S(O)$_2$N(R$^3$)— or —(R$^3$)NS(O)$_2$— (wherein R$^3$ is as defined for formula (I)), the group —(EZ)' in the compound of formula (III) is suitably —S(O)$_2$L or —N(R$^3$)H respectively (wherein L is a leaving group as defined above and R$^3$ is as defined for formula (I)) or a protected form thereof The compound of formula (IV) formed after reaction with the appropriate compound of formula (II) may then be treated with a compound of formula HN(R$^3$)—Z or L—S(O)$_2$—Z respectively (wherein L is a leaving group as defined above and R$^3$ and Z are as defined for formula (I)), typically in an inert solvent, such as a halogenated hydrocarbon for example dichloromethane, in the presence of an organic base, such as a trialkylamine, for example, triethylamine, at a moderate or reduced temperature, for example, in the range –30° C. to 50° C., suitably at ambient temperature or below;

(i) When E is to be —C(O)N(R$^3$)— or —(R$^3$)NC(O)— (wherein R$^3$ is as defined for formula (I)), the group —(EZ)' in the compound of formula (III) is suitably a carboxylic acid derivative or an amine respectively, as defined above. The compound of formula (IV) formed after reaction with the appropriate compound of formula (II) may then be treated with a compound of formula Z—NR$^3$H or Z—C(O)L respectively (wherein Z and R$^3$ are as defined for formula (I) and L is a leaving group as defined above), typically under the conditions described for conversion (i)(b) above. For example, when E is to be —C(O)NH—, the group —(EZ)' in the compound of formula (III) is suitably —COCl and may be reacted with a compound of formula Z—NH$_2$ (wherein Z is as defined for formula (I)).

(j) When E is to be —(R$^3$)NC(O)N(R$^4$)— (wherein R$^3$ and R$^4$ are as defined for formula (I)). The group —(EZ)' in the compound of formula (III) is suitably an isocyanate or —N(R$^3$)H group. The compound of formula (IV) formed after reaction with the appropriate compound of formula (II) may then be treated with a compound of formula Z—NHR$^4$ or Z—NCO respectively (wherein Z and R$^4$ are as defined for formula (I)), typically under the conditions described for conversion (i)(a) above. The resulting urea group may optionally be N-alkylated according to conventional methods to give the desired—(R$^3$)NC(O)N (R$^4$)Z group (wherein Z, R$^3$, and R$^4$ are as defined for formula (I)).

Optional conversion (iv) may be carried out as follows: Conversion of a compound of formula (I) to a corresponding salt may be effected by reaction with the appropriate acid or base. Conversion to a physiologically functional derivative, such as an ester, may be carried out by methods well known to a skilled man or readily available from the chemical literature.

Alternatively, group (WX)'— in the compound of formula (II) and/or group —(EZ)' in the compound of formula (III) may be converted to the respective group W—X— or —E—Z (as defined for formula (I)), or a protected form thereof before reacting the compounds of formulae (II) and (III) together to form the compound of formula (IV) (as defined for formula (I)). Such conversions may be effected by carrying out reactions analogous to those described in (a) to (j) above.

Compounds of formula (II) in which (WX)'—is a precursor for the group W—X—(as discussed above); for example, an isocyanate, carboxylic acid derivative, amine, or hydroxyl group; are commercially available or may be prepared by methods well known to those skilled in the art or methods readily available from the chemical literature. For example, where the compound of formula (II) required is a substitued aniline, it may be commercially available, or be prepared from the corresponding commercially available nitro compound by reduction, for example, by catalytic hydrogenation, in an inert solvent, for example, in the presence of palladium on charcoal or by chemical reduction, for example, with zinc dust.

Compounds of formula (III) in which—(EZ)' is a precursor for the group —E—Z (as discussed above; for example, a halogen, hydroxyalkyl, thioalkyl, carboxylic acid derivatively, sulphonic acid derivative, amine, or isocyanate group; are commercially available or may be prepared by methods well known to those skilled in the art or methods readily available from the chemical literature.

The reagents used to convert (WX)'— and —(EZ)' into W—X— and —E—Z respectively (as described above) are all commercially available or may be prepared by methods well known to those skilled in the art or methods available from the chemical literature.

At any stage of the process, certain functional groups may be chemically protected to prevent them being altered during chemical reaction at a different functional group on the molecule, as is well known to those skilled in the art. For example, where (WX)'— in the compound of formula (II) is an amine, it may be preferable to protect it (for example, with an alkoxycarbonyl group, such as tert-butoxycarbonyl), with subsequent deprotection by any appropriate method (for example, by acid hydrolysis). Other such methods of protection and deprotection are well known to those skilled in the art.

The present invention also provides novel intermediates of formula (II), as defined above; particularly a compound selected from:

N-(2-Bromo-4,6-difluorophenyl)pivalamide,
N-[2,4-Difluoro (trimethylsilylethyl)phenyl]pivalamide.
N-(2,4-Difluoro-6(ethynylphenyl)pivalamide; and
N-(2-Bromo-4,6difluorophenyl)pivalamide.

The present invention also provides novel intermediates of formula (III), as defined above, particularly a compound selected from:

3-(4-Benzyloxyphenyl) glutaric acid;
4-(4-Benzyloxyphenyl) glutarimide;
4-(4-Hydroxyphenyl) glutarimide;
Methyl 2-(4-methoxyphenyl)-2-methylpropanoate;
2-(4-Hydroxyphenyl)-2-methylpropanoic acid;
Methyl 2-(4-hydroxyphenyl)-2-methylpropanoate;
3-(4-Bromophenyl) glutaric acid;
4-(4-Bromophenyl) glutarimide, 4-(4Iodophenyl) glutarimide;
4-(4-Bromophenyl)-4-hydroxytetrahydropyran;
4-(4-Bromophenyl)-4-methoxytetrahydropyran;
4-(4-Trimethylsilylethynylphenyl)-4-methoxytetrahydropyran;
4-(4-Ethynylphenyl)-4-methoxytetrahydropyran;
Ethyl 2-(4-iodophenoxy)-2-methylpropanoate;
Ethyl (4-bromophenyl)ethanoate;
Ethyl 2-(4-bromophenyl)-2-methylpropanoate; and
Ethyl 2-(4-iodophenyl)-2-methylpropanoate.

The present invention also provides novel intermediates of formula (IV), as defined above; particularly a compound selected from:

2,4-Difluoro-6-[4-(2,6-dioxo-4-piperidinyl)phenoxy]-5-nitrobenzene;
2,4-Difluoro-6-[4-(2,6-dioxo-4-piperidinyl)phenoxy]-5-aminobenzene;
2-Fluoro-6-(4-trifluoromethoxyphenoxy) aniline;
Methyl 2-{4-[3,5-difluoro-2-nitrophenoxy]phenyl}-2-methylpropanoate; and
Methyl 2-{4-[2-amino-3,5-difluorophenoxy]phenyl}-2-methylpropanoate.

Certain compounds of formula (I) are also useful as intermediates in the preparation of other compounds of formula (I), for example a compound selected from:

Methyl 2-[4-(3,5-difluoro-2-pivalamidophenoxy)phenyl]2-melthylpropanoate;
2-[4-(3,5-Difluoro-2-pivalamidophenoxy)phenyl]-2-methylpropanoic acid;
Ethyl 2-[4-(3,5-difluoro-2-pivalamidophenylethynyl) phenoxy]-2-methylpropanoate;
2-[4-(3,5-Difluoro-2-pivalamidophenylethynyl)phenoxy]-2-methylpropanoic acid;
Ethyl 2-[4-(3,5-difluoro-2-pivalamidophenylethynyl) phenyl]-2-methyl propanoate; and
2-[4-(3,5-Difluoro-2-pivalamidophenylethynyl)phenyl]-2-methyl propanoic acid.

For a better understanding of the invention, the following Examples are given by way of illustration. All final products analysed correctly and gave nmr spectra consistent with the assigned structures.

SYNTHETIC EXAMPLE 1

Preparation of N-{2,4-Difluoro-6-[4-(2,6-dioxo-4-piperidinyl)phenoxy]phenyl}-pivalamide (a) 3-(4-Benzyloxyphenyl) glutaric acid 4-Benzyloxybenzaldehyde (50.0 g, Aldrich), ethyl acetoacetate (61.31 g, Aldrich), and piperidine (4.01 lg) were reacted together overnight. The resulting mixture was refluxed for 3–4 hours with ethanol (400 ml) and sodium methoxide (63.63 g).

On removal of the solvent in vacuo, the residue was washed twice with diethyl ether, and filtered. The solid was taken up in water (500 ml), filtered, and the filtrate acidified with concentrated HCl to give a yellow precipitate. Recrystallisation from ethyl acetate gave the title product.

Microanalysis: $C_{18}H_{18}O_5$% found (calculated) C69.59 (68.79), H 5.81 (5.77), N 0.05 (0.00).

(b) 4-(4-Benzyloxyphenyl)glutarimide

The product from Example 1(a) (10.0 g) was dissolved in 0.88 ammonia solution, then dried in vacuo. The residue was heated at 200–210° C. for 14 hours until $NH_3$ evolution had ceased and reaction was complete. On cooling, the reaction mixture was recrystallised from ethyl acetate to give the title product as a beige solid.

Microanalysis: $C_{18}H_{17}NO_3$ C 73.82 (73.20), H 6.22 (5.80), N 4.68 (4.74).

(c) 4-(4-Hydroxyphenyl)glutarimide

The product from Example 1(b) (2.76 g) was mixed with ethyl acetate (150 ml), and palladium on charcoal (500 mg) was added. The mixture was treated with $H_2$ at atmospheric pressure until gas uptake ceased and reaction was complete. The reaction mixture was filtered through Hyflo (Trademark) and the solvent was removed from the filtrate in vacuo to give the crude title product as a white solid, which was then recrystallised from ethanol.

Thin Layer Chromatography ($SiO_2$; Dichloromethane/ethanol 19:1): Rf0.33

(d) 2,4-Difluoro-6-[4-(2,6-dioxo-4-piperidinyl)phenoxy]-5-nitrobenzene

A solution of the product from Example 1(c) (10 g) was added slowly to a suspension of washed sodium hydride (117 mg) in tetrahydrofuran (THF). When the reaction was complete, the resulting suspension was concentrated to half volume and then added slowly to a solution of 2,4,6-trifluoronitrobenzene (1.29 g, Aldrich) in N,N-dimethylformamide (DMF). After 30 minutes at room temperature, the reaction was quenched with water and extracted 3 times with ethyl acetate. The combined organic phases were washed with water then dried over $MgSO_4$, filtered, and the solvent was removed in vacuo to give the crude title compound as a pale yellow solid which was then purified by flash column chromatography on silica, eluting with ethyl acetate/methanol (99,1).

(e) 2,4-Difluoro-6-[4-(2,6-Dioxo-4-Piperidinyl)Phenoxy]-5-Aminobenzene

To a mixture of the product from Example 1(d) (620 mg) in THF (15 ml), was added palladium on charcoal (60 mg) and 30% aqueous sodium hypophosphite (30 ml). The reaction was stirred for 2–3 hours, then filtered through Hyflo, poured into water then extracted twice with ethyl acetate. The combined organic phases were dried on $MgSO_4$, filtered, and the solvent was removed in vacuo to yield a white solid. Purification by flash column chromatography on silica, eluting with dichloromethane/methanol (19:1) afforded the title product.

(f) N-{2,4-Difluoro-6-[4-(2,6-Dioxo-4-piperidinyl) Phenoxy|Phenyl}Pivalamide

To a solution of the product from Example 1(e) (340 mg) in THF (10 ml) was added triethylamine (124 mg) and pivaloyl chloride (148 mg, Aldrich). The reaction was stirred overnight at room temperature, with the exclusion of moisture. After filtration through Hyflo, the filtrate was evaporated in vacuo to give an oil. The oil was dissolved in ethyl acetate and washed successively with water (×2), saturated $NaHCO_3$ (×2), then water (×2). The organic layer was dried over $MgSO_4$, filtered and the solvent removed in vacuo. After trituration with ethyl acetate/hexane/ether and removal of the solvent in vacuo, the crude title product was obtained as a white solid. Purification by preparative HPLC on silica, eluting with hexane/ethanol (9:1) afforded pure title product, mp 172° C.

SYNTHETIC EXAMPLE 2

Preparation of N-[2-Fluoro-6-(4-Trifluoromethoxyphenoxy)Phenyl|Pivalamide (a) 2-Fluoro-6-(4-Trifluoromethoxyphenoxy)Nitrobenzene To a solution of trifluoromethoxyphenol (35.0 g, Lancaster) in methanol was added a solution of potassium-t-butoxide (22.48 g) in methanol (total volume of solvent 150 ml). The reaction was stirred at room temperature for 30 mins., then the solvent was removed in vacuo to give the phenolate as an off-white solid.

The phenolate was dissolved in DMF (φml) and added slowly to a solution of 2,6-difluoronitrobenzene (34.39 g, Aldrich) in DMF (100 ml). After stirring overnight at room temperature, the reaction was poured into dilute NaOH and extracted 3 times with diethyl ether. The combined ethereal fractions were washed sequentially with dilute NaOH (×2), then water (×2), dried over MgSO$_4$, and the solvent removed in vacuo to give the title product.

(b) 2-Fluoro-6-(4-Trifluoromethoxyphenoxy)Aniline

To a solution of the product from Example 2a (30.0 g) in THF (150 ml) was added 10% palladium on charcoal (500 mg) then sodium phosphinate (100 g) in water (200 ml). Cooling was used to keep the reaction under control. After 1 hour the reaction mixture was filtered through Hyflo, the filtrate poured into water then extracted twice with dichloromethane. The combined organic phases were washed twice with water then dried on MgSO$_4$, filtered and the solvent removed in vacuo to give a pale yellow oil. Purification by flash column chromatography on silica, eluting with hexane/ethyl acetate (4:1) afforded the title compound.

Thin Layer Chromatography (SiO$_2$; Hexane/Ethyl Acetate 4:1) : Rf 0.48

(c) N-|2-Fluoro-6-(4-Trifluoromethoxyphenoxy) Phenyl] Pivalamide

To a solution of the product from Example 2(b) (20.0 g) in diethyl ether (100 ml), was added triethylamine (8.46 g), then a solution of pivaloyl chloride (10.08 g, Aldrich) in diethyl ether (100 ml). The reaction was stirred at room temperature overnight, then filtered. The filtrate was washed twice with water, then twice with saturated NaHCO$_3$, then twice with water. The organic phase was dried over MgSO$_4$, filtered then the solvent was removed in vacuo to give the crude product as a fawn solid. Recrystallisation from hexane/ethyl acetate (9:1) afforded the title compound as a white solid.

$^1$H-NMR (d$_6$-DMSO)δ : 8.9 (s, 1H , NH ), 7.35 (d, 2H, ArH), 7.35 (m, 1H ArH), 7.20 (td, 1H, ArH), 7.0 (m, 1H, ArH), 6.98 (d, 2H ArH), and 1.0 (s, 9H, $^t$Bu).

SYNTHETIC EXAMPLE 3

Preparation of N-{2,4-Difluoro-6-[4-(1-Carbamoyl-1-Methylethyl) Phenoxy|Phenyl}-Pivalamide (a) Methyl 2-(4-Methoxyphenyl)-2-Methylpropanoate.

To a stirred slurry of sodium hydride (22.4 g) in ethylene glycol dimethyl ether (250 ml) under N$_2$ was added a solution of methyl 4-methoxyphenylacetate (25 g, Aldrich) and methyl iodide (35 ml, Aldrich) in ethylene glycol dimethyl ether (50 ml) over approx. 15 minutes. Refluxing was continued overnight before most of the solvent was removed by distillation at reduced pressure. The resulting solid was cooled in an ice bath and diethyl ether (250 ml) added. After stirring, water (150 ml) was slowly added, before the two layers were separated. The ether layer was extracted with water (2×150 ml) before being dried (MgSO4) and the solvent removed in vacuo to give an orange oil. Purification was by distillation to give the title compound as a colourless oil (19.5 g) ; b.pt. 74° C. at 0.12 lm/Hg.

(b) 2-(4-Hydroxyphenyl)-2-Methylpropanoic Acid

The product from Example 3(a) (10.0 g) was dissolved in dichloromethane (100 ml) at −700° C. A solution of boron tribromide (1M in DCM ; 82 ml, Aldrich) was added dropwise through an air condenser. A calcium chloride tube was then fitted and the reaction left stirring overnight to attain room temperature. From this mixture was obtained a brown solution which was hydrolysed by shaking with water (150 ml). Diethyl ether (500 ml) was then added and the organic layer separated. The organic layer was extracted with 2M NaOH (250 ml) and then this extract neutralised with 2M HCL This combined layer was extracted into diethyl ether (300 ml) which was dried (MgSO$_4$) and then the solvent removed in vacuo to give the title compound as a crude brown oil (7.73 g).

(c) Methyl 2-(4-Hydroxyphenyl)-2-Methylpropanoate

The product from Example 3(b) (7.72 g) was dissolved up in methanol at room temperature. To this was added p-toluenesulphonic acid (0.25 g) and the reaction heated to reflux overnight. On completion the methanol was removed by distillation and the residue taken up in diethyl ether (200 ml). The diethyl ether layer was washed with water (200 ml) and dried (MgSO4) before the solvent was removed in vacuo to give a pale brown solid. Purification was by chromatography on silica (Merck) eluting with DCM diethyl ether (95:5) to give the title compound as a white solid (4.32 g).

(d) Methyl 2-{4-[3,5Difluoro-2-Nitrophenoxy]Phenyl}-2-methylpropanoate

The product from Example 3(c) (4.00 g) was treated with potassium methoxide (1.47 g) in dimethylformamide (DMF) (80 ml) and stirred at room temperature for 1 hour. To this was added 2,4,6-trifluoronitrobenzene (3.72 g, Aldrich) and the reaction left to stir overnight. On completion the reaction was poured into water (800 ml) and extracted with diethyl ether (2×250 ml). The organics were combined and washed with water (250 ml) and then dried (MgSO4). After filtering, the solvent was removed in vacuo to give a yellow oil. Purification was by chromatography on silica eluting with diethyl ether 40/60 petrol (1:2) to give two major components, i.e. the ortho and para substituted products. The desired ortho title compound was thus retained (2.2 g).

(e) Methyl 2-{4-[2-Amino-3,5-Difluorophenoxy]Phenyl}-2-Methylpropanoate

The product from Example 3(d) (2.02 g) was dissolved up in tetrahydrofuran (THT) (70 ml) with vigorous stirring. To this was added Pd/C (10%) (0.2 g) followed by NaH$_2$PO$_2$.×H$_2$O solution (30% aqueous solution, 80 ml) and the reaction stirred at room temperature for 3 hours. On completion the reaction was filtered through 'Hyflo' and added to water (150 ml). This aqueous layer was extracted with diethyl ether (2×150 ml) which was then dried (MgSO4) and the solvent removed in vacuo to give the title compound as a dark brown oil (1.31 g).

(f) Methyl 2-[4-(3,5-Difluoro-2-Pivalamidophenoxy/Phenyl]-2-Methylpropanoate

The product from 3(e) was dissolved in DCM (30 ml) in an ice bath. To this was added 4-dimethyl-aminopyridine (DMAP) (50 mg, Aldrich) and pyridine (0.4 g) and the ice bath removed, allowing the reaction to warm to room temperature. Pivaloyl chloride (0.6 g, Aldrich) in DCM (30 ml) was added dropwise and the reaction left to sir under N$_2$ overnight. On completion the mixture was added to diethyl ether (200 ml) and washed with 8% citric acid (2×50 ml), water (150 ml) and then dried (MgSO$_4$). The solution was filtered and the solvent removed in vacuo to give a brown oil. Purification was by chromatography on silica eluting with diethyl ether: 40/60 petrol (1:1) to give a solid with was recrystallised from hot 40/60 petrol to give the title compound as a white solid (0.60 g); m.p. 103°–104° C.

(g) 2-[4-(3,5-Difluoro-2-Pivalamidophenoxy)Phenyl]-2-Methylpropanoic Acid

The product from Example 3(f) (0.51 g) was dissolved up in methanol (8 ml) at room temperature with vigorous sting To this was added sodium hydroxide (60.5 mg) in water (8 ml) and the reaction mixture refluxed for 4 hours. On completion the mixture was cooled and the methanol removed by distillation. The resulting aqueous layer was acidified to pH=1 using 2M HCl. The white solid was filtered off and washed thoroughly with water to give the title product (0.45 g) ; m.p. 168°–170° C.

(h) N-{2,4-Difluoro-6-[4-(1-Carbamoyl-1-Methylethyl) Phenoxy]Phenyl}Pivalamide

The product from Example 3(g) (0.32 g) and triethylamine (0.12 ml) were stirred in terahydrofuran (THF) (10 ml) in an ice bath. To this was added methylchloroformate (0.08 g, Aldrich) rapidly with continuous sting. After 1 hour anhydrous $NH_3$ gas was passed through the reaction for approx. 5 minutes. The mixture was then removed form the ice bath, stirred at room temperature for 1 hour then left standing overnight. On completion the triethylamine and THF were removed in vacuo, the residue taken up in dichloromethane (150 ml) and then washed with 8% citric acid (100 ml). The acid layer was extracted with DCM and the organic layers combined and washed with NaHC03 (100 ml) and water (100 ml) before being dried ($MgSO_4$). After filtering, the solvent was removed in vacuo to give a colourless oil. Purification was by triturating with 40/60 petrol and a trace of diethyl ether to give the title compound as a white solid (0.25 g); m.p. 169°–170° C.

$^1$H-NMR ($CDCl_3$) δ: 7.20 (q, 4H, Ar—H), 6.80 (s, 1H, NH), 6.70 (m, 1H Ar—H), 6.45 (m, 1H, Ar—H), 5.25 (wide s, 2H, $NH_2$), 1.60 (s, 6H, 2×methyl), 1.20 (s, 9H, 'Bu).

SYNTHETIC EXAMPLE 4

Preparation of 1-[4-(3,5-Difluoro-2-Pivalamidophenoxy)Phenyl]Cyclopentane-1-Nitrile (a) 4-(p-Hydroxyphenyl)-1-Cyclopentanecarboxylic Acid A solution of 1-(p-methoxyphenyl)-1-cyclopentanecarboxylic acid (5 g, Aldrich) in dry dichloromethane (DCM) (100 ml), cooled to −780° C., was treated (dropwise) under nitrogen with boron tribromide (100 ml) in dry DCM. The mixture was stirred for thirty minutes at −780° C., then at room temperature (RT) overnight. The reaction mixture was slowly poured into ice, DCM was separated, and the aqueous phase was extracted with DCM (3×20 ml). The organic extracts were combined, washed with saturated brine, dried over sodium sulphate, filtered and evaporated in vacuo to afford the phenol as a white solid.

$^1$H NMR (DMSO): δ 5 1.5–1.8 (m, $_6$H,$CH_2CH_2CH_2C$ $H_2$); 2.4–2.6 (m, 2H, $CH_2CH_2CH_2CH_2$); 6.7 (dd, 2H, aryl); 7.1(dd, 2H aryl); 9.3 (broad singlet, 1HI, OH); 12.0 (broad singlet, 1H COOH).

(b) 1-(p-Hydroxyphenyl)-1Cyclopentanecarboxamide

1-Hydroxybenzotriazole (3.68 g, Aldrich), 1-Ethyl-3-(3-Dimethylaminopropyl)-carbodiimide hydrochloride (5.28 g Sigma) and N-Methylmorpholine (2.78 g, Aldrich) were added, under nitrogen, to a stirred solution of the product from Example 4(a) (5.0 g) in dry tetrahydrofuran (THF). The mixture was stirred at RT for four hours, then slowly added to liquid ammonia (excess) at −60° C. After one hour, the mixture was warmed to RT and stirred overnight.

THF was evaporated, and the residue was partitioned between water ($H_2O$) and ethyl acetate (EtOAc). The product was extracted into EtOAc (3×20 ml). The extracts were combined, washed once with saturated sodium bicarbonate, once with $H_2O$, once with IM hydrochloric acid (HCI), once with $H_2O$, and once with semi-saturated brine. After drying over $Na_2SO_4$, and filtration, the filtrate was evaporated in vacuo to afford the crude product as a white solid. Recrystallization from cyclohexane and DCM gave t he pure amide as a white solid.

$^1$H NMR (DMSO) δ 1.5–1.7 (m, 6H, $CH_2CH_2CH_2C$ $H_2$); 2.4 (m, 2H, $CH_2CH_2CH_2CH_2$); 6.6–6.7 (m, 3H, 2aryl, 1NH); 6.8 (broad singlet 1H, NH); 7.1 (dd, 2H, aryl); 9.2 (s, 1H OH).

(c) 1-[4-(3,5-Difluoro-2-Nitrophenoxy)Phenyl] Cyclopentane-1-carboxamide and 1-[4-(3,5-Difluoro-4-Nitrophenoxy)Phenyl]Cyclopentane-1-carboxamide.

The product from Example 4(b) (0.55 g), in dry acetonitrile (ACN) (10 ml), was treated at 0° C. under nitrogen with sodium hydride. After fifteen minutes, the mixture was warmed to RT and stirred for another hour. The white precipitate which ensued was taken up in a small amount of dimethylformamide (DMF), and then slowly added at 0° C. to trifluoronitrobenzene (0.52 g, Aldrich). The resulting mixture was stirred at 0° C. for two hours, then at RT overnight. Solvent was evaporated in vacuo, and the residue was partitioned between $H_2O$ and pet ether (40–60). The organic phase was separated, and the aqueous phase was extracted with EtOAc (3×12 ml). This was combined, washed with brine, dried over sodium sulphate, filtered and evaporated in vacuo to give the crude product as a light yellow oil. Purification by chromatography ($SiO_2$) using EtOAc/cyclohexane (1:1) as the eluent gave the title products as a yellow solid.

The products were obtained as a mixture of two isomers.

(d) 1-[4-(3,5-Difluoro-2-Aminophenoxy)Phenyl] Cyclopentane-1-Carboxamide and 1-[(4-(3,5-Difluoro-4Aminophenoxy)Phenyl]Cyclopentane-1-Carboxamide.

The adduct from Example 4(c) (0.52 g) in ethanol (EtOH) (25 ml) was treated with 10% palladium on activated charcoal (0.06 g), and the suspension was hydrogenated at RT and atmospheric pressure for three hours. The catalyst was removed by filtration and the filtrate was evaporated in vacuo to give a light brown oil.

The products were obtained as a mixture of two isomers.

(e) 1-[4-(3,5-Difluoro-2-Pivalamidophenoxy)Phenyl] Cyclopentane-1-Nitrile

A solution of the product from Example 4(d) (0.51 g) and triethylamine (0.17 g, Aldrich) in DCM was treated, dropwise, at 0° C., under nitrogen, with pivaloyl chloride. The reaction mixture was stirred at 0° C. for fifteen minutes, then at RT overnight.

DCM was evaporated, and the residue was taken up in water and extracted with EtOAc (3×25 ml). The organic extracts were combined, washed once with saturated sodium bicarbonate, once with $H_2O$ and once with semi-saturated brine. The organic phase was dried over $Na_2SO_4$, filtered and evaporated under reduced pressure to afford the crude product as a light brown oil. Purification by chromatography ($SiO_2$) using EtOAc/cyclohexane 1:3 as the eluent gave the product as an oil, which was crystallised from water and methanol to afford the title product as a white solid, mp 103°–5° C.

SYNTHETIC EXAMPLE 5

Preparation of N-{2,4-Difluoro-6-[4-(2,6-Dioxo-4-Piperidinyl)Phenylethyl]Phenyl}- Pivalamide (a) N-(2-Bromo-4-Difluorophenyl)Pivalamide 2-Bromo-4,6-difluoroaniline (50 g, Aldrich) in dry tetrahydrofuran (THF) (100 mi) was treated at 0° C., under nitrogen, with pivaloyl chloride (34.7 g), N-methylmorpholine (29.13 g, Aldrich) and dimethylaminopyridine (1.42 g, Aldrich). The mixture was warmed to room temperature, and was left stirring overnight. The THF was evaporated under reduced pressure, and the residue was taken up in water, washed three times with ethyl acetate. The extracts were combined, washed once with 1N HC1, once with water, and once with brine. The organic solution was dried over sodium sulphate, filtered, and the filtrate was evaporated in vacuo to afford the amide as a white solid. Recrystallization from ethyl acetate and cyclohexane gave the product as a white solid.

$^1$H NMR (CDCl$_3$):δ1.35 (s,9H,C(CH$_3$)$_3$); 6.9–7.0(m, 2H,NH and Ph); 7.2–7.3 (m, 1H, aryl).

(b) N-[2,4-Difluoro-6-(Trimethylsilylethynyl)Phenyl] Pivalamide

A solution of the product from Example 5(a) (24.2 g) and (trimethylsilyl)acetylene (83 ml, Aldrich) in trimethylamine (TEA) (40 ml) was degassed and placed under a nitrogen atmosphere. To this solution was added copper (1) iodide (0.04 g, Aldrich) and tetrakis (triphenylphosphine) palladium (0.81 g). After stirring at room temperature for fifteen minutes, the reaction mixture was heated at 60°–70° C. for five hours. On cooling, TEA was evaporated under reduced pressure, and the residue was partitioned between dichloromethane (DCM) and water. The DCM was separated, and the aqueous phase was extracted twice with DCM. The organic extracts were combined, washed with brine, dried over sodium sulphate, filtered and evaporated in vacuo. The crude product was purified by flash chromatograph (SiO$_2$), eluted with cyclohexane/ethylacetate 2:1. The product was obtained as a light brown solid on evaporation of solvent.

$^1$H NMR (CDCl$_3$):δ 0.3 (s,9H,SiC(CH$_3$)$_3$); 1.35 (s,9H C(CH$_3$)$_3$); 6.8–7.0 (m, 2H,Ph); 7, 1 (broad s, 1H, NH)

(c) N-(2,4-Difluoro-6-Ethynylphenyl)Pivalamide

The product from Example 5(b) (20 g) in dry THF was treated under nitrogen with tetrabutylammonium fluoride solution 1M in THF (62 ml, Aldrich). The mixture was stirred at room temperature for 1 hour and THF was evaporated under reduced pressure. The residue was partitioned between water and DCM, the organic phase was separated and the aqueous phase was extracted twice with DCM. The organic extracts were combined, washed once with brine, dried over sodium sulphate, filtered and the filtrate was evaporated in vacuo to afford the crude product. Filtration through silica gel using DCM as the eluent gave the title product as an off white solid.

$^1$H NMR (CDCl$_3$): δ 1.35 (s,9H,C(CH$_3$)$_3$); 3.4(s, 1H, CCH; 6.8–7.05 (m, 2H, Ph); 7.1 (broad s, 1H, NH)

(d) 3-(4-Bromophenyl) Glutaric acid

4-Bromobenzaldehyde (50.0 g, Aldrich), ethylacetoacetate (70.3 g, Aldrich), and piperidine (4.6 g, Fisons) were stirred together overnight. The resulting mixture was refluxed in the presence of ethanol (500 ml) and sodium methoxide (73.9 g) for 3–4 hours. On cooling, the solvent was concentrated in vacuo, and the sodium salt, a yellow/orange solid, was filtered, washed twice with diethyl ether and taken up in water. Acidification with concentrated HCl gave a light yellow solid, which upon recrystallization from ethyl acetate gave the title product as an off white solid.

$^1$H-NMR (DMSO): δ 2.4–2.7 (m, 4H, 2×CH$_2$CH); 3.2–3.4 (m, 1H CH$_2$CH); 7.2–7.5 (dd, 4H aryl) 12.1 (broad s, 2H, 2×OH).

(e) 4-(4-Bromophenyl) Glutarimide

The product from Example 5(d) (20 g) was taken up in 0.88 ammonia solution, then heated at 100° C. until all the ammonia solution had evaporated. The resultant residue was heated at 200°–210° C. for 2–4 hours until NH$_3$ evolution had ceased, (pH 5). On cooling, the reaction mixture was taken up in hot ethyl acetate from which the product crystallized. This was removed by filtration, and the mother liquor was concentrated in vacuo from which the second crop (impure by thin layer chromatography) was obtained. This was filtered and dissolved in 0.88 ammonia solution, and the reaction was repeated as above to afford the pure title product as a brown solid.

$^1$H NMR (DMSO): δ 2.6–2.9 (m, 4H, 2×CH$_2$CH); 3.4 (m, 1H CH$_2$CH); 7.3–7.6 (dd, aryl); 10.9 (s, 1H, NH).

(f) 4(4-Iodophenyl) Glutarimide

The product from Example 5(e) (1.9 g) in 1,3-Dimethyl-3,4,5,6-tetrahydro-2-(1H) pyrimidione (50 ml, Aldrich) was treated under nitrogen with copper iodide (6.8 g Aldrich) and potassium iodide (17.7 g). The mixture was heated at ca. 160°–180° C. for 6–8 hours. On cooling the reaction mixture was quenched with dilute HCl. The aqueous phase was decanted and diluted with water. The dark brown sludge was discarded, and the aqueous phase was washed three times with diethyl ether. The ethereal extracts were combined, washed once with brine, dried over sodium sulphate, filtered, and the filtrate was concentrated in vacuo. Trituration under cyclohexane gave the iodide as an off white solid.

Thin layer chromatography (SiO$_2$; Ethyl acetate/cyclohexane 1:1): R$_f$ 0.26.

(g) N-{2,4-Difluoro-6-[2,6-Dioxo-4-Piperidinyl)Phenylethenyl|Phenyl}Pivalamide

The iodide from Example 5(f) (0.63 g) and the alkyne from Example 5(c) (0.53 g), in piperidine (8 ml, Fisons) were degassed and stirred at room temperature under nitrogen and then treated with tetrakis (triphenylphosphine) palladium (012 g, Aldrich). The reaction mixture was stirred for one hour, and then quenched with saturated ammonium chloride solution. The yellow solid which ensued was filtered, taken up in ethyl acetate, dried over sodium sulphate, filtered and evaporated under reduced pressure. Purification by flash chromatograph (SiO$_2$) with ethylacetate cyclohexane 1:1 as the eluent gave the product as an off white solid. Recrystallization from water and methanol gave the product as a white solid, mp 114°–8° C.

Microanalysis: C$_{24}$H$_{22}$F$_2$N$_2$O$_3$ Calculated: C 67.91:H 5.22:N 6.6 Found: C 67.45:H 5.20:N 6.54.

SYNTHETIC EXAMPLE 6

Preparation of N-{2,4-Difluoro-6-[4-(4-Methoxytetrahydropyran-4-yl)Phenylethenyl|-Phenyl}Pivalamide (a) 4-(4-Bromophenyl)-4-Hydroxytetrahydropyran 1,4-Dibromobenzene (1 17.96 g, Aldrich) in tetrahydrofuran (THF) (700 ml) was cooled to −70° C. under nitrogen and butylithium (175 ml) was added dropwise. After stirring the mixture for 15 minutes, tetrahydro-4H-pyran4-one (25 g, Aldrich) in the THF (300 ml) was added. The reaction was left for 2 hours before being allowed to warm to room temperature. The reaction mixture was shaken with 5% citric acid (800 ml), then extracted with diethyl ether (3×600 ml). The combined organic layers were washed with water (500 ml), and dried over MgSO$_4$. Removal of the solvent from the filtrate gave the crude tide product as an off-white solid.

(b) 4-(4-Bromophenyl)-4-Methoxytetrahydropyran

The product from Example 6(a) (64.28 g) in N,N-dimethylformamide (DMF) (400 ml) was added to ether washed sodium hydride (60% dispersion, 10.4 g), the reaction mixture was then stirred under N$_2$ for 1 hour. Methyl iodide (30.9 ml) in DMF was then added dropwise, and the reaction left stirring overnight. On completion, the reaction was quenched with water (3000 ml) and extracted with ether (3×1000 ml). The combined organic extracts were washed with 2M HCL (1000 ml) and then water (1000 ml), and dried on MgSO$_4$. Removal of the solvent from the filtrate gave the crude title product as a red/orange oil which crystallised on standing. Purification by chromatography on silica gel, eluting with 40°–60° petroleum ether/diethyl ether (2:1) afforded the title product as a white crystalline solid (30.18 g).

(c) 4-(4-Trimethylsilylethynylphenyl)-4-Methoxytetrahydropyran

The product from Example 6(b) (30 g), (trimethylsilyl) acetylene (12.8 g), and piperidine (100 ml) were mixed together under nitrogen for 10 minutes. Copper (I) iodide (0.13 g) and triphenylphosphine (0.18 g) were then added followed by palladium (O) tetra(triphenylphosphine) (3×0.11 g) with the exclusion of light. The reaction was heated for 4 hours at 105° C., with the exclusion of light. On completion, the reaction mixture was poured into n-pentane (500 ml) and mixed with water (400 ml). The separated aqueous layer was back extracted with n-pentane (500ml) and the combined organic phases were washed with a mixture of 2M HCl/saturated $NH_4Cl$ (400 ml:200 ml). The washed organic phase was sequentially washed with saturated $NH_4Cl$ (200 ml), water (600 ml), and brine (600 ml) and finally dried over $MgSO_4$. Removal of the solvent from the filtrate in vacuo gave the crude tide product as a yellow/orange oil (31.52 g).

(d) 4-Ethynylphenyl)-4Methoxytetrahydropyran

The product from Example 6(c) (31.5 g) was dissolved in diethyl ether and stirred under nitrogen at 0° C. To this was added tetrabutylammonium fluoride on silica (1.1 mmol F⁻/g gel, Fluka) (100 g), and the reaction was stirred for 2 hours at 0°. On completion, the reaction mire was filtered, washing the gel with excess diethyl ether. Removal of the solvent from the filtrate gave the crude tide product as an orange oil/gum. Purification by chromatography on silica gel, eluting with dichloromethane/diethyl ether (95:5) afforded the title product as a pale yellow solid (18.01 g).

(e) N-(2-Bromo-4,6-Difluorophenyl) Pivalamide

2-Bromo-4,6-difluoroaniline (10.4 g, Aldrich) was dissolved in dichloromethane (75 ml) and treated with pyridine (4.63 g) in an ice bath. 4-Dimethylaminopyridine (0.61 g) was then added and the mixture was allowed to warn to room temperature. After dropwise addition of pivaloyl chloride (7.23 g, BDH), the reaction was stirred for 5 hours. On completion, the mixture was added to diethyl ether (250 ml), washed twice with 2M HCI (250 ml) and the resulting organic layer was treated with saturated $NaHCO_3$ (2×250 ml). The organic layer was washed with water (250 ml), and dried over $MgSO_4$. Removal of the solvent from the filtrate gave the crude title product as a white solid (13.40 g).

(f) N-{2,4-Difluoro-6|Methoxytetrahydropyran-4-yl) Phenylethynyl|Phenyl}- Pivalamide The product from Example 6(d) (15 g) and the product from Example 3(e) were dissolved in DMF (250 ml) with triethylamine (300ml) and stirred for 20 minutes under $N_2$. To this solution, was added palladium (O) tetra (triphenylphosphine) (0.76 g), triphenylphosphine (0.29 g), and copper (I) iodide (0.21 g), and stirring was continued for 20 minutes. The reaction was then heated to 100° C. for 8 hours. On completion, the reaction mixture was poured into water (3000 ml) and extracted sequentailly with hexan (2×600 ml), then diethyl ether (600 ml). The ether extract was treated with hexane to remove dissolved palladium salts, then the organic phases were combined, washed with aqueous citric acid and treated with ½ mole equivalent of triethylamine. The organic layer was separated and washed with water (100 ml) and brine (1000 ml), before being dried on $MgSO_4$. Removal of the solvent in vacuo from the filtrate gave the crude title product as a red/brown oil. Purification by chromatography on silica, eluting with diethyl ether/ 40°–60° petroleum ether gave the title product as a white solid; mp 77°–79° C.

SYNTHETIC EXAMPLE 7

Preparation of N-{2,4-Difluoro-6-|4-Tetrahydropyran-4-ylthio)Phenylethynyl|Phenyl}-Pivalamide (a) 4-Tetrahydropyran-4-ylthio)Bromobenzene 4-Bromothiophenol (15.7 g, Lancaster) was treated with potassium carbonate (22.9 g) in dimethylformamide (DMF) (200 ml). This was stirred at room temperature for 1 hour. To this was added 4-chloropyran (10 g, Aldrich) dropwise followed by potassium iodide (approx. 2 g). The resulting mixture heated to ~700° C. and left stirring overnight.

The reaction mixture was poured into water (2000 ml) and extracted with diethyl ether (3×300 ml). The organic layers were combined and washed with water (2×250 ml) and then dried (MgSO4). After filtering and removal of solvent in vacuo, a brown oil was obtained which was purified on silica (Merck) eluting with diethyl ether: 40/60 petrol (1:1) to give the title product as a yellow crystalline solid (18.91 g).

(b) 4-(Tetrahydropyran-4-ylthio)Phenylacetylene

The product from Example 7(a) (4.0 g) was mixed with trimethylsilylacetylene (1.76 g, Aldrich) and piperidene (12 ml) under $N_2$ for 10 minutes. Added to this were the catalysts copper iodide (17 mg, Aldrich),triphenylphosphine (23 mg, Aldrich) and tetrakistriphenylphosphine palladium (o) (15 mg, Aldrich). Two further additions of the later catalyst were made at 20 minute intervals (2×15 mg). All such additions as well as the reaction were carried out with the exclusion of light. Reaction was heated to 105° C. for 5 hours. On completion the reaction was poured into diethyl ether (150 ml) and mixed with water (200 ml). The organic phase was removed while the aqueous was extracted with diethyl ether (2×150 ml). The organics were combined and washed with a 2:1% mix of 2M HCl/$NH_4Cl$ (100:50 ml) and separated. The organics were then washed with water (100 ml),brine (100 ml) and then dried ($MgSO_4$). The solvent was removed in vacuo to give a brown oil.

This oil (4.35 g) was dissolved in dry diethyl ether (120 ml)-and stirred under anhydrous $N_2$ at 0° C. To this was added tetrabutylammoniumfluoride (TBAF) on silica gel (13.3 g, Fluka) and the reaction stirred at this temperature for 2 hours. On completion,the TBAF was filtered off and washed with dry diethyl ether and the filtrate concentrated in vacuo to give an orange oil. Purification was achieved by chromatography on silica eluting with diethyl ether: 40/60 petrol (1:2) to give the tide compound as a pale yellow solid (2.5 g)

Microanalysis: $C_{13}H_{15}OS$ % found (calculated) C 77.88 (79.19), H 6–63 (6.89).

(c) N-{2,4-Difluoro-6-|4-(Tetrahydropyran-4-ylthio) Phenylethynyl|Phenyl}- Pivalamide The product from Example 6(e) (1.27 g) and the product from Example 7(b) (1.0 g) were mixed with $NEt_3$ (20 ml) and DMF (15 ml) and stirred under $N_2$. To this were added the catalysts tetrakistriphenylphosphine palladium (O) (50 mg), triphenylphosphine (17.5 mg) and copper iodide (13.1 mg) and the solution stirred for 20 minutes. The reaction was then heated to 100° C. for 2 hours. On completion the mixture was poured into water (150 ml), extracted with diethyl ether (3×150 ml). The organic phases were combined and washed with aqueous citric acid (0.5 mole equ. of NEt$_3$). The organic layer was removed and washed with water (100 ml) be fore being dried (MgSO$_4$), filtered and the solvent removed in vacuo to give a brown oil. Purification was by chromatography on silica eluting with diethyl ether: 40/60 petrol (2:1) to afford the title compound as a yellow solid (350 mg) ; mp 148°–149° C.

SYNTHETIC EXAMPLE 8

Preparation of N-{6-[4-(1-Carbamoyl-1-Methylethoxy)Phenylethynyl]2,4-Difluoro-Phenyl}Pivalamide (a) Ethyl 2-(4-Iodophenoxy-2-Methylpropanoate Sodium ethoxide was prepared by disposing sodium metal (0.63 g) in absolute ethanol (60 ml) at room temperature. To this solution was added 4-iodophenol (6.0 g, Aldrich) and ethyl 2-bromo-2-methylpropanoate (5.6 g, Aldrich) and the mixture heated to reflux for 6 h.

On completion, the mixture was poured into water (100 ml), 1M NaOH (150 ml) and ethyl acetate (200 ml). The organic layer was quickly removed and washed with 2M HCl (150 ml) followed by sodium bicarbonate (100 ml) and water (100 ml) before being dried (MgSO$_4$). After filtering the solvent was removed in vacuo to give a yellow oil which was purified on silica gel eluting with diethyl ether: 40/60 petrol (1:2) to afford the tide product as a colourless oil (5.60 g).

(b) Ethyl 2-[4-(3,5-Difluoro-2-Pivalamidophenylethynyl) Phenoxy]- 2-Methylpropanoate The product from Example 5(c) (0.04 g) and the product from Example 8(a) (0.56 g) together with triethylamine (10 ml) and dimethylformamide (0.5 ml) were stirred together under N$_2$ at room temperature. With the reaction flask completely excluded from light, the catalysts CuI (3 mg, Aldrich) and bis(triphenyl phosphine) palladium (II) chloride (24 mg. Aldrich) were added and the reaction stirred at room temperature for 3 h.

On completion, the triethylamine was removed in vacuo and the residue taken up in diethyl ether (200 ml), before being washed with water (200 ml), the two layers were separated and the aqueous re-extracted with ethyl acetate (150 ml). The combined organics were washed with 5% citric acid (150 ml) and water (150 ml) before being dried (MgSO$_4$). After filtering the solvent was removed in vacuo to give the brown oily solid which was purified on silica gel eluting with diethyl ether: 40/60 petrol (1:1) to afford the title product as a yellow oil (0.62 g).

(c) 2-[4-(3,5-Difluoro-2-Pivalamidophenylethynyl) Phenoxy]- 2-methylpropanoic acid The product from Example 8(b) (together with a quantity of an earlier batch) (Total=0.92 g) was dissolved up in methanol with stirring at room temperature. To this was added NaOH (100 mg) in water (15 ml) dropwise. The reaction mixture was then refluxed from 5 h.

On completion, the solvent was removed in vacuo and the aqeuous layer acidified to pH=1 with 2M HCl The resulting solid was extracted into ether (100 ml) and dried (MgSO$_4$). In order to remove an impurity that still remained, the solid was extracted into 1M NaOH and washed with diethyl ether (100 ml). This basic To was reacidified with 2M HCl, the product extracted into diethyl ether (100 ml) and dried (MgSO$_4$). After filtering, the solvent was removed in vacuo to give the title product as the crude yellow oil (0.84 g).

(d) N-{6-[4-(1-Carbamoyl-1-Methylethoxy)Phenylethynyl]-2,4-Difluorophenyl}- Pivalamide The product from Example 8(c) was dissolved up in tetrahydrofuran (30 ml) and triethylamine (0.28 ml, Aldrich) and then cooled in an ice bath. To this was added methylchloroformate (0.2 g, Aldrich) rapidly with continuous stirring. After 1 h, anhydrous NH$_3$ was passed through the solution for approx. 5 min. The mixture was then removed from the cooling bath, stirred at room temperature for 1 h. and then left standing overnight.

On completion, the tetrahydrofuran and triethylamine were removed in vacuo and the residue taken up in dichloromethane (200 ml). This was washed with 5% citric acid (150 ml) and then this layer re-extracted with dichloromethane (200 ml). The combined organic layers were washed successively with sodium bicarbonate (100 ml) and water (100 ml) before being dried (MgSO$_4$). After filtering the solvent was removed in vacuo to give a pale yellow oil which was triturated with 40/60 petroleum ether to give a pale yellow solid. Purification was achieved on silica gel 60 (Merck) eluting with diethyl ether to afford the title compound as a white solid (0.62 g) ; m.p. 89°–90° C.

$_1$H-NMR (CDCl$_3$) δ:7.45 (m,2H ArH), 7.15 (s, 1H, NH), 7.05 (m, 1H, ArH), 6.95 (m, 2H, ArH), 6.50 & 5.40 (s, 2H, NH$_2$), 1.60 (s, 6H, methyl-H), 1.35 (s, 9H $^t$Bu).

SYNTHETIC EXAMPLE 9

Preparation of N-{6-[4-(1-Carbamoyl-1-Methylethyl)Phenylethynyl]2,4-Difluoro-Phenyl}Pivalamide (a) Ethyl (4-Bromophenyl)Ethanoate.

4-Bromophenylacetic acid (45 g, Aldrich) was dissolved up in ethanol (300 ml) at room temperature along with p-toluenesulphonic acid (0.75 g). The reaction mixture was then stirred overnight.

The ethanol was then removed in vacuo and the residue taken up in diethyl ether (200 ml). The diethyl ether layer was then washed with water (200 ml) and the aqueous layer re-extracted with diethyl ether (200 ml). The combined organics were then dried (MgSO$_4$), filtered and the solvent removed in vacuo to give the title product as a pale yellow oil (50.27 g).

(b) Ethyl 2-(4-Bromophenyl)-2-Methylpropanoate.

NaH (60% dispersion in mineral oil) (33.12 g, Aldrich ) was washed with dry diethyl ether before being formed into a slurry with ethylene glycol diethyl ether (200 ml). To this was added the product from Example 9(a) (50.25 g) and methyl iodide (51.5 ml Aldrich) dropwise in more ethylene glycol dimethyl ether (150 ml). This was then left to reflux overnight under N$_2$.

The ethylene glycol dimethyl ether was then removed by distillation at reduced pressure. The resulting solid was then cooled in an ice bath and diethyl ether (400ml) was added. After stirring, water (300 ml) was added, stirred again and then the two layers separated.

The diethyl ether layer was extracted with water (2×300 ml) before being dried (MgSO$_4$). After filtering the solvent was removed in vacuo to give a yellow oil which was purified by distillation to give the title product as a colourless oil (35.5 g) ; b.pt. 84°–860° C. at 0.2 mm/Hg.

(c) Ethyl 2-(4-Iodophenyl)-2-Methylpropanoate.

The product from Example 9(b) (35.5 g), nickel bromide (0.81 g, Aldrich) and potassium iodide (109 g) were stirred together in dimethylformamide (DMF) (250 ml) under N$_2$ before tributyl phosphine (3.3 ml, Aldrich) was added at room temperature. The reaction was then heated to reflux for 18 h.

The reaction mixture was allowed to cool to room temperature and added to water (1200 ml) before being extracted into ethyl acetate (500 ml). The layers were separated and the aqueous re-extracted with ethyl acetate (2×400 ml). The organics were combined and washed with 2M HCl (400 ml) and saturated sodium sulphite solution (200 ml) before being dried (MgSO$_4$). After filtration the solvent was removed in vacuo to give the title product as a pale yellow oil (40.10 g).

(d) Ethyl 2-[4-(3,5 Difluoro-2-Pivalamidophenylethynyl)Phenyl]-2-Methyl Propanoate.

The product from Example 5(c) (12.1 1g) and the product from Example 9(c) (12.0 g) were stirred together in triethylamine (120 ml, Aldrich) and dimethylformamide (25 ml) under N$_2$ (free of O$_2$ by passage through Fieser's solution). The mixture was stirred at room temperature with N$_2$ bubbled through the solution until all the solids had dissolved. With the reaction flask completely excluded from light, bis(triphenylphosphine)palladium(II) chloride (0.76 g, Aldrich) and copper iodide (0.36 g, Aldrich) were added and the reaction stirred at room temperature for 24 h.

On completion, triethylamine was removed in vacuo and the residue partitioned between saturated ammonium chloride (350 ml) and ethyl acetate (400 ml). The organics were separated and washed with 2M HCl (250 ml), 20% sodium thiosulphate solution (250 ml) and brine (250 ml). The organic layer was then dried (MgSO$_4$), filtered and the solvent removed in vacuo to give a brown oil which was purified on silica gel, eluting with diethyl ether : 40/60 petrol ether (1:1) to afford the title product as a yellow solid (10.10 g).

(e) 2-[4-(3,5-Difluoro-2-Pivalamidophenylethynyl)Phenyl]-2-Methyl Propanoic Acid The product from Example 9(d) (10.1 g) was dissolved in methanol (100 ml) at room temperature. To this was added NaOH (1.10 g) in water (100 ml) dropwise with rapid stirring. The reaction mixture was then refluxed for 5 h. before being stirred at room temperature overnight.

On completion of reaction, the solvent was removed in vacuo and the resulting aqueous layer, first washed with diethyl ether (250 ml) and then acidified to pH=1 with 2M HCl. The solidified product was extracted into diethyl ether (300 ml), which was dried (MgSO$_4$), then filtered and the solvent removed in vacuo to give the crude title product as a pale yellow solid (7.8 g)

(f) N-{6-[4-(1-Carbamoyl-1-Methylethyl)Phenylethynyl]-2,4-Difluorophenyl}Pivalamide:

The product from Example 9(e) was dissolved in tetrahydrofuran (150 ml) and triethylamine (2.8 ml, Aldrich) and then cooled in an ice bath. To this was added methylchloroformate (1.89 g, Aldrich) rapidly with continuous stirring. After 1 h., anhydrous NH$_3$ was passed through the solution for approx. 15 min. The mixture was then removed from the cooling bath, stirred at room temperature for 1 h and then left standing overnight.

On completion, the tetrahydrofuran and triethylamine were removed in vacuo and the residue taken up in ethyl acetate (350 ml). This was washed successively with 5% citric acid (250 ml), sodium bicarbonate (250 ml) and water (250 ml) before being dried (NaSO$_4$). After filtration the solvent was removed in vacuo to give a pale yellow oil which was recrystallised from ethyl acetate and 40/60 petroleum ether to afford the title compound as a white solid (4.51 g); m.p. 170°–172° C.

SYNTHETIC EXAMPLE 10

Preparation of Trans-N-(2,4-Difluoro-6-{2-[4-(4-Methoxytetrahydropyran-4-yl)Phenyl]-ethenyl}Phenyl)Pivalamide The product from Example 6 (3.0 g) was dissolved in dimethylsulphoxide and Pd(dba)$_2$ (200 mg) was added. The mixture was treated with H$_2$ at atmospheric pressure until gas uptake ceased. On completion, the reaction was added to water (500 ml) and extracted with ethyl acetate (2×400 ml). The combined organic extracts were washed with water (2×300 ml) and then dried on MgSO$_4$, and filtered. Removal of the solvent in vacuo gave a yellow oil which was dissolved in diethyl ether, treated with charcoal, then filtered through, Hyflo. Removal of the solvent from the filtrate gave the crude title product. Precipitation from ethyl acetate/40°–60° petroleum ether afforded the title product as a white solid; mp 150°–151° C.

SYNTHETIC EXAMPLE 11

Preparation of N-(2,4Difluoro-6-{2-[4-(4-Methoxytetrahydropyran-4-yl)Phenyl]Ethyl}-Phenyl)Pivalamide To a solution of the product from Example 6 (3.0 g) in ethanol, was added 10% palladium on charcoal (300 mg). The reaction mixture was treated with H$_2$ at atmospheric pressure until uptake ceased. On completion, the reaction was filtered and the solvent was removed from the filtrate in vacuo to give a green oil. Traces of remaining catalyst were removed by filtration to give a yellow oil. The oil was precipitated from ethyl acetate/40°–60° petroleum ether to afford the title compound as a white solid, mp 147°–148°C.

SYNTHETIC EXAMPLES 12–69

The following compounds of formula (I) were prepared in a manner analogous to the methods of Synthetic Examples 1 to 4.

12) N-[2-Fluoro-6-(4-trans-cyclohexylsulfamoylphenoxy)phenyl]pivalamide, mp 176°–178° C.;

13) N-[2-Fluoro-6-(3-trifluoromethoxyphenoxy)phenyl] pivalamide, mp 84°–85° C.;

14) N-{2,4-Difluoro-6-[4-(4-methoxytetrahydropyran-4-yl) phenoxy]phenyl}pivalamide, mp 145°–146° C.;

15) 2-[4-(3,5-Difluoro-2-pivalamidophenoxy)phenyl]-2-methylpropanoic acid, mp 168°–170° C.;

16) Methyl 2-[4-(3,5-difluoro-2-pivalamidophenoxy)phenyl]-2-methyl propanoate, mp 103°4° C.;

17) 1-[4-(3-Fluoro-2-pivalamidophenoxy)phenyl] cyclopentane-1-carboxylic acid, mp 152°–4° C.;

18) 1-[4-(3-Fluoro-2-pivalamidophenoxy)phenyl] cyclopentane-1-carboxamide, mp 175°–60° C.;

19) N-[2,4-Difluoro-6-(4-piperidinylcarbonylphenoxy) phenyl]pivalamide hemihydrate, mp 55°6° C.;

20) N-{2-Fluoro-6-[4-phenylsulfamoyl)phenoxy] phenyl}pivalamide, mp 179°–181° C.;

21) N-{2-Fluoro-6-[4-(N-tert-butylsulfamoyl)phenoxy| phenyl}pivalamide, mp 197°–199° C.;

22) 2,4-difluoro-6-[4-(4-morpholinocarbonyl)phenoxyl] phenylpivalamide, mp 63°–65° C.;

23) 2,2-Dimethyl-N-{2,4-difluoro-6-[4-(2,6-dioxopiperidin-4yl)phenoxy]phenyl}butanamide, 0.8 hydrate, mp 180°–1° C.;

24) N-{2-Fluoro-6-[4-(1-imidazolyl)phenoxy| phenyl}pivalamide, mp 207°–9° C.;

25) N-{2,4-Difluoro-6-[3-fluoro-5-(4-methoxy-4-pyranyl) phenoxy]phenyl}- pivalamide, mp 102°–103° C.

26) N-[2-(4-Chlorophenoxy)-6-fluorophenyl]pivalamide, mp 145°–6° C.;

27) N-{2-[4-(2,2-Diethoxyethoxy)phenoxy]-6-fluorophenyl}pivalamide, mp 63°–5° C.;

28) N-{2-Fluoro-6-[4-(2,2-dimethoxyethoxy)phenoxy] phenyl}pivalamide, mp 86°–7° C.;

29) N-{2-Fluoro-6-[4-(2-methoxyethoxymethoxy)phenoxy| phenyl}pivalamide, Microanalysis C$_{21}$H$_{26}$FNO$_5$: C 64.56 (64.45), H 6.84 (6.65), N 3.41 (3.58);

30) 4-(3-Fluoro-2-pivalamidophenoxy)phenyl-1-methylethanesulphonate, mp 130°–2° C.;
31) 4-(3-Fluoro-2-pivalamidophenoxy)phenylpivalate, mp 121°–123° C.;
32) N-[2-Fluoro-6-(4methylphenoxy)phenyl]pivalamide, mp 115°–6° C.;
33) N-[2-(4-Chlorophenoxy)-6-fluorophenyl] cyclopentanecarboxamide, mp 130°–1° C.;
34) N-[2-Fluoro-6-(4-methoxyphenoxy)phenyl]pivalamide;
35) [4-(3,5-Difluoro-4-pivalamidophenoxy)phenyl] piperidin-2,6-dione, mp 177°–178° C.;
36) Ethyl 4-(3,5-difluoro-2-pivalamidophenoxy)benzoate, mp 110°–112° C.;
37) N-tert-Butyl-N'-{4-[(2-pivalamido)3-fluorophenoxy]phenyl}urea, mp 176°–178° C.;
38) N-{2-fluoro-6-[4-(2,6-dimethyoxybenzoylamino) phenoxy]phenyl}pivalamide, mp 194°–196° C.;
39) N-[2-Fluoro-6-(4-pivalamidophenoxy)phenyl] pivalamide, mp 187°–189° C.;
40) N-[2-Fluoro-6-(4-phenylsulphonylaminophenoxy) phenyl]pivalamide, mp 237°–240° C.;
41) N-{2-Fluoro-6-[4-benzamidophenoxy] phenyl}pivalamide, mp 264°–267° C.;
42) N-{2-[4(Isopropylsulfonyl)phenoxy]-6-fluorophenyl}pivalamide, mp 153°–154° C.;
43) N-{2-Fluoro-6-[4-(isopropylsulfinyl)phenoxy] phenyl}pivalamide, mp 155°–156° C.;
44) N-[2-Fluoro-6-(4-tert-butoxycarbonylaminophenoxy) pivalamide, mp 209°–214° C.;
45) N-[2-Fluoro-6-(4-trifluorophenoxy)phenyl]pivalamide, mp 155° C.;
46) N-{2-[4-(2,2-Dimethyoxyethyl)phenoxy]-3-trifluoromethylphenyl}pivalamide;
47) 3-[2-(4-Chlorophenoxy)-6-fluorophenyl]-1,1-dimethylurea, mp 143°–40° C.;
48) N-[2-(4-Chlorophenoxy)phenyl]pivalamide, mp 90°–1° C.;

The following compounds of formula (I) were prepared in a manner analogous to the methods of Synthetic Examples 5 to 9.

49) N-2,4-Difluoro-6-{[3-chloro-4-(2,6-dioxo-4-piperidyl) phenyl]ethynyl}- phenyl)pivalamide, mp 178°–180° C.;
50) N-{2,4-Difluoro-6-[4-(3-methoxy-8-oxa-[3.2.1 ]-bicyclooctan-3-yl)phenyl- ethynyl]phenyl}pivalamide, mp 64°–68° C.;
51) N-{2,4-Difluoro-6-[4-(4-hydroxytetrahydropyran-4-yl) phenylethynyl]phenyl}- pivalamide, mp 85°–91° C.;
52) 1-[4-(3,5-Difluoro-2-pivalamidophenylethynyl)phenyl] cyclopentane-1- carboxamide hydrate, mp 195°–7° C.;
53) Methyl 2-{4-[3,5-difluoro-2-(2,2-dimethylpropanamido)phenyl]ethynyl}phenyl-2- methyl propanoate, mp 71°–30° C.;
54) N-{2,4-Difluoro-6-[4-(tetrahydropyran-4-yl sulphony) phenylethynyl]phenyl}pivalamide, mp 255°–6° C.;
55) N-{2,4-Difluoro-6-[4-(tetrahydropyran-4-yl) phenylethynyl]phenyl}propanamide, mp 173°–5° C.;
56) N-{2,4-Difluoro-6-[4-(4-methoxyethoxymethoxytetrahydropyran-4-yl)phenyl-ethynyl]phenyl}pivalamide, mp 96°–97° C.;
57) 2,4-Difluoro-6-{[3-(4-methoxytetrahydropyran)phenyl] ethynyl}- pivalamide;
58) N-{2,4-Difluoro-6-[4-(5,6-dihydro-2H-pyran-4-yl) phenylethynyl]phenyl}- pivalamide, mp 165°–167° C.;
59) 4,6Difluoro-2-[4-(1,3,6-trioxaheptyl)phenylethynyl) phenyl]pivalamide, mp 86°–8° C.;
60) 3-[4-(3,5-Difluoro-2-Pivalamidophenylethynyl)phenyl] -N,N-pentamethylene- pentadiamide, 0.5 hydrate, mp 90° C. (softens);
61) N-{2,4Difluoro-6-[2-(4-hydroxy-3,5-dimethylphenyl) ethyl]phenyl}isobutyramide, mp 140°–141° C.;
62) N-{2,4-Difluoro-6-[2(4-isopropylsulphonyloxy)ethyl] phenyl}mp 111°–2° C.;
63) N-{2,4-Difluoro-6-[2-(4-hydroxy-3,5-dimethylphenyl) ethyl]phenyl}isobutyramide, mp 187°–188° C.;
64) 2-{4-[3,5-Difluoro-2-(2,2-dimethylpropanamido) phenyl]ethynyl}phenyl-2- methylpropanoic acid, mp 110°–111° C.;

The following compounds of formula (I) were prepared using the processes described above.

65) N-[2-(4-Chlorobenzyloxy)-4,6-difluorophenyl] pivalamide, mp 98°–9° C.;
66) (+–)-N-{2-Fluoro-6-[1-(4-chlorophenyl)ethoxy] phenyl}pivalamide, mp 110°–111° C.;
67) N-{2-Fluoro-6-[4-(2,2-dimethoxyethoxy)phenylthio] phenyl}pivalamide;
68) N-[2-Fluoro-6-(4-methoxyphenylsulfonyl)phenyl] pivalamide, mp 179°–181 ° C.;
69) N-[2-Fluoro-6-(4-methoxyphenylthio)phenyl] pivalamide, mp 101°–103° C.;

PHARMACEUTICAL FORMULATION EXAMPLES

In the following Examples, the "active ingredient" is as hereinbefore defined, preferably one of the compounds of Synthetic Examples 1 to 69.

| Tablet | |
|---|---|
| | Per tablet |
| Active Ingredient (sub 250 μm) | 5.0 mg |
| Lactose | 82.0 mg |
| Starch | 10.0 mg |
| Povidone | 2.0 mg |
| Magnesium Stearate | 1.0 mg |

Mix together the active ingredient, lactose and starch. Granulate the powders using a solution of povidone in purified water. Dry the granules, add the magnesium stearate and compress to produce 100 mg tablets.

| Controlled release tablet | |
|---|---|
| | Per tablet |
| Active ingredient (sub 250 μm) | 500 mg |
| Hydroxypropylmethylcellulose (Methocel K4M Premium) | 112 mg |
| Lactose B.P. | 53 mg |
| Povidone B.P.C. | 28 mg |
| Magnesium Stearate | 7 mg |
| | 700 mg |

The formulation may be prepared by wet granulation of the first three ingredients with the solution of povidone, followed by addition of the magnesium stearate and compression.

| Capsule | |
|---|---|
| | Per capsule |
| Active ingredient (sub 250 μm) | 250 mg |
| Lactose B.P. | 143 mg |

-continued

| Capsule | Per capsule |
|---|---|
| Sodium Starch Glycollate | 25 mg |
| Magnesium Stearate | 2 mg |
| | 420 mg |

Capsules may be prepared by admixing the ingredients of the formulation and filling two-part hard gelatin capsules with the resulting mixture.

| Controlled release capsule | Per capsule |
|---|---|
| Active ingredient | 250 mg |
| Microcrystalline Cellulose | 125 mg |
| Lactose BP | 125 mg |
| Ethyl Cellulose | 13 mg |
| | 513 mg |

The controlled-release capsule formulation may be prepared by extruding a mixture of the first three ingredients, then spheronising and drying the extrudate. The dried pellets are coated with the ethyl cellulose as a controlled-release membrane and filled into two-part hard gelatin capsules.

| Powder capsule for inhalation | Per capsule |
|---|---|
| Active Ingredient (0.5–5.0 μm powder) | 4.0mg |
| Lactose (30–90 μm powder) | 46.0mg |

The powders were mixed until homogeneous and filled into suitably sized hard gelatin capsules (SOmg per capsule).

| Injectable solution | |
|---|---|
| Active Ingredient | 10.0 mg |
| Water for Injections B.P. | to 1.0 ml |

The active ingredient was dissolved in half of the Water for Injections and then made up to volume and sterilised by filtration. The resulting solution was distributed into ampoules under aseptic conditions.

| Intramuscular injection formulation | |
|---|---|
| Active ingredient | 0.20 g |
| Benzyl Alcohol | 0.10 g |
| Glycofurol 75 | 1.45 g |
| Water for Injection | q.s. to 3.00 ml |

The active ingredient is dissolved in the glycofurol. The benzyl alcohol is added and dissolved, then water added to 3 ml. The solution is filtered through a sterile micropore filter and sealed in sterile 3 ml glass vials.

| Inhalation aerosol | |
|---|---|
| Active Ingredient (0.5–5.0 μm powder) | 200 mg |
| Sorbitan Trioleate | 100 mg |
| Saccharin Sodium (0.5–7.0 μm powder) | 5 mg |
| Menthol | 2 mg |
| Trichlorofluoromethane | 4.2 g |
| Dichlorodifluoromethane | to 10.0 ml |

The sorbitan trioleate and menthol were dissolved in the trichloro-fluoromethane. The saccharin sodium and active ingredient were dispersed in the mixture which was then transferred to a suitable aerosol canister and the dichlorofluoromethane injected through the valve system. This composition provides 2 mg of active ingredient in each 100 μl dose.

| Syrup formulation | |
|---|---|
| Active ingredient | 0.25 g |
| Sorbitol Solution | 1.50 g |
| Glycerol | 1.00 g |
| Sodium Benzoate | 0.0050 g |
| Flavour | 0.0125 ml |
| Purified Water | q.s. to 5.0 ml |

The sodium benzoate is dissolved in a portion of the purified water and the sorbitol solution added. The active ingredient is added and dissolved. The resulting solution is mixed with the glycerol and then made up to the required volume with the purified water.

| Suppository formulation | Per suppository |
|---|---|
| Active ingredient (63 μm)* | 250 mg |
| Hard Fat, BP (Witepsol H15 - Dynamit Nobel) | 1770 mg |
| | 2020 mg |

*The active ingredient is used as a powder wherein at least 90% of the particles are of 63 μm diameter or less.

One-fifth of the Witepsol H15 is melted in a steam-jacketed pan at a maximum temperature of 45° C. The active ingredient is sifted through a 200μm sieve and added to the molten base with mixing, using a Silverson fitted with a cutting head, until a smooth dispersion is achieved. Maintaining the mixture at 45° C., the remaining Witepsol H15 is added to the suspension which is stirred until homogenous. The entire suspension is then passed through a 250 μm stainless steel screen and, with continuous stirring, allowed to cool to 40° C. At a temperature of 38°–40° C., 2.0 μg aliquots of the mixture are filled into suitable plastic moulds and the suppositories allowed to cool to room temperature.

| Pessary formulation | Per pessary |
|---|---|
| Active ingredient (63 μm) | 250 mg |
| Anhydrous Dextrose | 380 mg |
| Potato Starch | 363 mg |
| Magnesium Stearate | 7 mg |
| | 1000 mg |

The ingredients are mixed directly and pessaries prepared by compression of the resulting mixture.

Biological Assay

In Vitro Inhibition of ACAT

The in vitro esterification of cholesterol in the presence of ACAT and the test compound was assayed radiometrically using [$^{14}$C]oleoyl CoA as substrate:

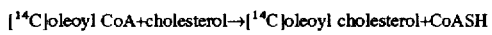

[$^{14}$C]oleoyl CoA+cholesterol→[$^{14}$C]oleoyl cholesterol+CoASH

The enzyme is membrane-associated in vivo. Microsomal protein is therefore used as the source of both ACAT and cholesterol. The compounds of the invention were tested against enzyme derived from human embryo 407 intestinal epithelial cell line.

[$^{14}$C]Oleoyl CoA was incubated with microsomal protein at 37° C., pH 70, in the presence of various concentrations of the test compound. After 4 minutes, the reaction was stopped by the addition of ice-cold chloroform/methanol containing a known amount of [$^3$H]oleoyl cholesterol to compensate for the loss of any [$^{14}$C] product. A known volume of the resulting lower phase, which contains lipidic material from the reaction, was dried, redissolved in hexane containing unlabelled oleoyl cholesterol (TLC marker) and run on a quantitative TLC plate (silica gel). The oleoyl cholesterol spot was visualised (iodine vapour), removed from the TLC plate and its radioactivity measured by scintillation counting.

A plot of ACAT inhibitory activity vs concentration was prepared for each test compound and the corresponding $IC_{50}$ determined. The compounds of Synthetic Examples 1 to 69 were all found to significantly inhibit ACAT. For example, the compounds of Examples 1 to 10 were all found to have an $IC_{50}$ of less than 10 μM.

We claim:

1. A compound of formula (I)

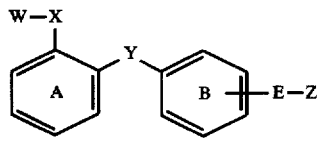

or a pharmaceutically acceptable salt, solvate, or physiologically functional derivative thereof, wherein:

W is hydrogen, or a $C_{1-12}$ hydrocarbyl group optionally substituted by one or more groups independently selected from halo, $C_{1-4}$ alkyl, $C_{1-4}$ alkoxy, hydroxy, $C_{1-4}$ haloalkyl $C_{1-4}$ haloalkoxy, and RC(O)— (wherein R is selected from hydrogen, $C_{1-4}$ alkyl $C_{1-4}$ alkoxy, hydroxy, $C_{1-4}$ haloalkyl, and $C_{1-4}$ haloalkoxy);

X is —NR$^1$C(O)NR$^2$—, —NR$^1$C(O)—, —NR$^1$C(O)O—, —C(O)NR$^2$—, or —OC(O)NR$^2$— (wherein R$^1$ and R$^2$ are independently selected from hydrogen, $C_{1-4}$ alkyl, and Y is a bond, $C_{2-4}$ alkynylene, $C_{2-4}$ alkenylene (cis or trans), $C_{1-4}$ alkylene, —(CH$_2$)$_n$—O—(CH$_2$)$_p$—, or —(CH$_2$)$_n$S(O)$_q$—(CH$_2$)$_p$—, (wherein n and p are integers independently selected from 0, 1, 2, 3, and 4; providing that n+p is not greater than 4; and q is an integer selected from 0, 1, and 2), and Y is optionally substituted by one or more groups independently selected from halo, $C_{1-4}$ alkyl, and $C_{1-4}$ haloalkyl;

E is a bond, $C_{1-4}$ alkylene, —(CH$_2$)$_r$O—(CH$_2$)$_s$—, —(CH$_2$)$_r$—S(O)$_t$—(CH$_2$)$_s$—, —(CH$_2$)$_r$C(O)—(CH$_2$)$_s$—— (wherein r and s are integers independently selected from 0, 1, 2, 3 and 4; providing that r+s is not greater than 4; and t is an integer selected from 0, 1, and 2), —OC(O)—, —C(O)O—, —S(O)$_2$N(R$^3$)—, —(R$^3$)NS (O)$_2$—, —C(O)N(R$^3$)—, —(R$^3$)NC(O)N(R$^4$)—, or —(R$^3$)NC(O)— (wherein R$^3$ and R$^4$ are independently selected from hydrogen, $C_{1-4}$ alkyl, and $C_{1-4}$ haloalkyl);

Z is an aliphatic heterocyclic ring system, and Z is optionally substituted by one or more groups independently selected from halo, cyano, —CO$_2$R$^6$, —C(O)NR$^6$R$^7$, —NR$^6$R$^7$ (wherein R$^6$ and R$^7$ are independently selected from hydrogen, $C_{1-4}$ alkyl, and $C_{1-4}$ haloalkyl), $C_{1-4}$ alkyl, $C_{1-4}$ haloalkyl, $C_{1-4}$ alkoxy, $C_{1-4}$ haloalkoxy, hydroxy, and $C_{2-8}$ polyether, phenyl rings A and B are optionally substituted by one or more groups independently selected from halo, $C_{1-4}$ alkyl, $C_{1-4}$ haloalkyl, $C_{1-4}$ alkoxy, $C_{1-4}$ haloalkoxy, hydroxy, cyano, R$^8$R$^9$NC(O)—, R$^8$C(O)N(R$^9$)—, R$^8$C (O)O—, and R$^8$C(O)— (wherein R$^8$ and R$^9$ are independently selected from hydrogen, $C_{1-4}$ alkyl, and $C_{1-4}$ haloalkyl).

2. A compound of formula (I) according to claim 1 wherein:

W is $C_{3-7}$ alkyl optionally substituted as described in claim 1;

X is —C(O)NR$^2$—, —NR$^1$C(O)—, or —NR$^1$C(O)NR$^2$— (wherein R$^1$ and R$^2$ are as defined in claim 1;

Y is ethylene, ethenylene, ethenylene, —O—, —S—, —CH$_2$O—, or —OCH$_2$—;

E is —O—, —OCH$_2$—, —CH$_2$O—, a bond, —C(O)N (R$^3$)—, —(R$^3$)NC(O)—, —S—, —S(O)—, —S(O)$_2$—, —R$^3$)NS(O)$_2$—, —S(O)$_2$N(R$^3$)—, —(R$^3$)NC(O)N(R$^4$)—, or —C(O)— (wherein R$^3$ and R$^4$ are as defined in claim 1); and Z is a 5— or 6—membered saturated heterocyclic ring and Z is optionally substituted as described in claim 1;

or a salt, solvate, or physiologically functional derivative thereof.

3. A compound of formula (I) according to claim 1 selected from:

N-{2,4-Difluoro-6-[4-(2,6-dioxo-4-piperidinyl) phenylethynyl]phenyl}pivalamide;

N-{2,4-Difluoro-6-[4-(4-methoxytetrahydropyran-4-yl) phenylethynyl]phenyl}- pivalamide;

N-{2,4-Difluoro-6-[4-(2,6-dioxo-4-piperidinyl)phenoxy] phenyl}pivalamide;

or a salt, solvate, or physiologically functional derivative thereof.

4. A pharmaceutical formulation comprising a compound of formula (I) (as defined in claim 1), or a pharmaceutically acceptable salt, solvate, or physiologically functional derivative thereof, and a pharmaceutically acceptable carrier or excipient.

5. A process for preparing a compound of formula (I) according to claim 1, or a salt, solvate, or physiologically functional derivative thereof; which comprises coupling a compound of formula (II) with a compound of formula (III);

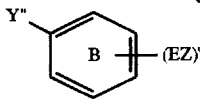

wherein,

Y and Y" are groups capable of reacting together to form the desired linkage Y (as defined for formula (I));

(WX)'— is either the group W—X— (wherein W and X are as defined for formula (I)), a protected form thereof, or a precursor for the said group W—X—;

—(EZ)' is either the group —E—Z (wherein E and Z are as defined for formula (I)), a protected form thereof or a precursor for the said group —E—Z;

and rings A and B are optionally substituted as described for formula (I);

to give either a compound of formula (I) or a compound of formula (IV):

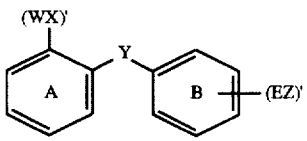

wherein Y is as defined for formula (I), (WX)'— and —(EZ)' are as defined for formulae (II) and (III) respectively (excluding combinations of (WX)'— and —(EZ)' which give a compound of formula (I)), and rings A and B are optionally substituted as described for formula (I);

followed by, (i) When (WX)'— in the compound of formula (II) is a precursor for the group W—X—, formation of the group W—X—; and/or (ii) When —(EZ)' in the compound of formula (III) is a precursor for the group —E—Z; formation of the group —E—Z; and/or (iii) Removal of any protecting groups; and/or (iv) Optional formation of a salt, solvate, or physiologically functional derivative of the resulting compound of formula (I), as discussed below or conversion to a different compound of formula (I).

6. A compound of formula (I) according to claim 1 wherein:

W is $C_{3\text{-}5}$alkyl;

X is —C(O)NH—;

Y is ethenylene or —O—;

E is —O—, or a bond;

Z is a 5- or 6-membered saturated heterocylic ring and Z is optionally substituted by one or more groups independently selected from the group consisting of halo, cyano, —$CO_2R^6$, —C(O)$NR^6R^7$, —$NR^6R^7$ wherein $R^6$ and $R^7$ are independently hydrogen, —$C_{1\text{-}4}$alkyl or $C_{1\text{-}4}$haloalkyl, $C_{1\text{-}4}$alkyl, $C_{1\text{-}4}$haloalkyl, $C_{1\text{-}4}$alkoxy, $C_{1\text{-}4}$haloalkoxy, hydroxy and $C_{2\text{-}8}$polyether.

7. A compound of formula (I) according to claim 2 wherein:

W is $C_{3\text{-}5}$alkyl;

X is —C(O)NH—;

Y is ethenylene or —O—;

E is —)—, or a bond;

Z is a 5- or 6-membered saturated heterocylic ring and Z is optionally substituted by one or more groups independently selected from the group consisting of halo, cyano, —$CO_2R^6$, —C(O)$NR^6R^7$, —$NR^6R^7$ wherein $R^6$ and $R^7$ are independently hydrogen, $C_{1\text{-}4}$alkyl or $C_{1\text{-}4}$haloalkyl, $C_{1\text{-}4}$alkyl, $C_{1\text{-}4}$haloalkyl, $C_{1\text{-}4}$alkoxy, $C_{1\text{-}4}$haloalkoxy, hydroxy and $C_{2\text{-}8}$ polyether.

8. A method for the prophylaxis or treatment of a clinical condition in a mammal, such as a human, for which an ACAT inhibitor is indicated, which comprises the administration to the mammal of a therapeutically effective amount of a compound of formula (I) or a pharmaceutically acceptable salt, solvate, or physiologically functional derivative thereof

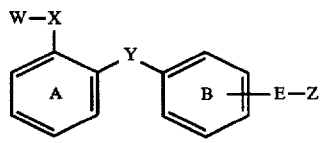

wherein:

W is hydrogen, or a $C_{1\text{-}12}$ hydrocarbyl group optionally substituted by one or more groups independently selected from halo, $C_{1\text{-}4}$ alkyl, $C_{1\text{-}4}$ alkoxy, hydroxy, $C_{1\text{-}4}$ haloalkyl, $C_{1\text{-}4}$ haloalkoxy, and RC(O)— (wherein R is selected from hydrogen, $C_{1\text{-}4}$ alkyl $C_{1\text{-}4}$ alkoxy, hydroxy, $C_{1\text{-}4}$ haloalkyl, and $C_{1\text{-}4}$ haloalkoxy);

X is —$NR^1$C(O)$NR^2$—, —$NR^1$C(O)—, —$NR^1$C(O)O—, —C(O)$NR^2$—, or —OC(O)$NR^2$—(wherein $R^1$ and $R^2$ are independently selected from hydrogen, $C_{1\text{-}4}$ alkyl, and $C_{1\text{-}4}$ haloalkyl);

Y is a bond, $C_{2\text{-}4}$ alkynylene, $C_{2\text{-}4}$ alkenylene (cis or trans), $C_{1\text{-}4}$ alkylene, —$(CH_2)_n$—O—$(CH_2)_p$—, or —$(CH_2)_n$—S(O)$_q$—$(CH_2)_p$—, (wherein n and p are integers independently selected from 0, 1, 2, 3, and 4; providing that n+p is not greater than 4; and q is an integer selected from 0, 1, and 2), and Y is optionally substituted by one or more groups independently selected from halo, $C_{1\text{-}4}$ alkyl, and $C_{1\text{-}4}$ haloalkyl;

E is a bond, $C_{1\text{-}4}$ alkylene, —$(CH_2)_r$O—$(CH_2)_s$—, —$(CH_2)_r$—S(O)$_t$—$(CH_2)_s$—, —$(CH_2)_r$—C(O)—$(CH_2)_s$— (wherein r and s are integers independently selected from 0, 1, 2, 3 and 4; providing that r+s is not greater than 4; and t is an integer selected from 0, 1, and 2), —OC(O)—, —C(O)O—, —S(O)$_2$N($R^3$)—, —($R^3$)NS(O)$_2$—, —C(O)N($R^3$)—, —($R^3$)NC(O)N($R^4$)—, or —($R^3$)NC(O)— (wherein $R^3$ and $R^4$ are independently selected from hydrogen, $C_{1\text{-}4}$ alkyl, and $C_{1\text{-}4}$ haloalkyl);

Z is an aliphatic heterocyclic ring system or heteroaromatic, and Z is optionally substituted by one or more groups independently selected from halo, cyano, —$CO_2R^6$, —C(O)$NR^6R^7$, —$NR^6R^7$ (wherein $R^6$ and $R^7$ are independently selected from hydrogen, $C_{1\text{-}4}$ alkyl, and $C_{1\text{-}4}$ haloalkyl), $C_{1\text{-}4}$ alkyl, $C_{1\text{-}4}$ haloalkyl, $C_{1\text{-}4}$ alkoxy, $C_{1\text{-}4}$ haloalkoxy, hydroxy, and $C_{2\text{-}8}$ polyether;

phenyl rings A and B are optionally substituted by one or more groups independently selected from halo, $C_{1\text{-}4}$ alkyl, $C_{1\text{-}4}$ haloalkyl, $C_{1\text{-}4}$alkoxy, $C_{\text{-}4}$ haloalkoxy, hydroxy, cyano, $R^8R^9$NC(O)—, $R^8$C(O)N($R^9$)—, $R^8$C(O)O—, and $R^8$C(O)— (wherein $R^8$ and $R^9$ are independently selected from hydrogen, $C_{1\text{-}4}$ alkyl, and $C_{1\text{-}4}$ haloalkyl);

provided that if Y is methylene, ethylene, or n-propylene, or —CH=CH—(cis or trans), then group —E—Z is not $C_{1\text{-}6}$ alkyl optionally substituted by one or more independently selected polar groups.

9. A method for the prophylaxis or treatment of a clinical condition in a mammal, such as a human, for which an ACAT inhibitor is indicated, which comprises the administration to the mammal of a therapeutically effective amount of a compound according to claim 1, or a pharmaceutically acceptable salt, solvate, or physiologically functional derivative thereof.

10. A method for the prophylaxis or treatment of a clinical condition in a mammal, such as a human, for which an ACAT inhibitor is indicated, which comprises the administration to the mammal of a therapeutically effective amount of a compound according to claim 2, or a pharmaceutically acceptable salt, solvate, or physiologically functional derivative thereof.

11. A method for the prophylaxis or treatment of a clinical condition in a mammal, such as a human, for which an ACAT inhibitor is indicated, which comprises the administration to the mammal of a therapeutically effective amount of a compound according to claim 3, or a pharmaceutically acceptable salt, solvate, or physiologically functional derivative thereof.

* * * * *